(12) United States Patent
Lee et al.

(10) Patent No.: US 11,925,581 B2
(45) Date of Patent: Mar. 12, 2024

(54) CAPSULOTOMY DEVICE

(71) Applicant: TI INC., Gyeonggi-do (KR)

(72) Inventors: Hong Jai Lee, Seoul (KR); Sung Hyuk Moon, Busan (KR); Jae Wook Yang, Busan (KR); Seung Jai Lee, Gyeonggi-do (KR); Sun Joon Hwang, Gyeonggi-do (KR); Hyun Jeong Kang, Gyeonggi-do (KR)

(73) Assignee: TI INC., Gyeonggi-Do (KR)

( * ) Notice: Subject to any disclaimer, the term of this patent is extended or adjusted under 35 U.S.C. 154(b) by 478 days.

(21) Appl. No.: 17/270,439

(22) PCT Filed: Aug. 23, 2019

(86) PCT No.: PCT/KR2019/010725
§ 371 (c)(1),
(2) Date: Feb. 23, 2021

(87) PCT Pub. No.: WO2020/040580
PCT Pub. Date: Feb. 27, 2020

(65) Prior Publication Data
US 2021/0212860 A1 Jul. 15, 2021

(30) Foreign Application Priority Data
Aug. 23, 2018 (KR) .................. 10-2018-0098682

(51) Int. Cl.
A61F 9/013 (2006.01)
(52) U.S. Cl.
CPC .................. A61F 9/0133 (2013.01)
(58) Field of Classification Search
CPC ............ A61F 9/00745; A61F 9/00754; A61F 9/00763; A61F 9/0133; A61F 2009/00889;
(Continued)

(56) References Cited

U.S. PATENT DOCUMENTS 4,481,948 A 11/1984 Sole
2010/0312252 A1* 12/2010 Jia .................. A61F 9/00754
606/29

(Continued)

FOREIGN PATENT DOCUMENTS

JP 2012-528676 11/2012
JP 2014-184332 10/2014
(Continued)

OTHER PUBLICATIONS

International Search Report for PCT/KR2019/010725 dated Nov. 28, 2019 and its English translation from WIPO (now published as WO2020/040580).

(Continued)

Primary Examiner — Robert A Lynch
(74) Attorney, Agent, or Firm — Ladas & Parry, LLP

(57) ABSTRACT

A capsulorhexis device is inserted into an incision site of a cornea to make an incision in an anterior capsule surrounding a crystalline lens. The capsulorhexis device includes a loop having elasticity and conductivity; a moving member having one end fixed and coupled to the loop; an insertion guide configured so that, while the incision is being made in the crystalline lens capsule, a front end thereof is inserted into the incision site of the cornea; and a housing having one end coupled to a rear end of the insertion guide, wherein the loop is housed in the housing and, to make the incision in the crystalline lens capsule, slides in the housing together with the moving member to pass through the insertion guide and be deployed into an anterior chamber of the eye.

14 Claims, 18 Drawing Sheets

(58) Field of Classification Search
CPC ............ A61B 10/0266; A61B 17/3205; A61B 17/32056; A61B 2018/1407; A61B 2018/141
See application file for complete search history.

(56) References Cited

U.S. PATENT DOCUMENTS

| | | | | |
|---|---|---|---|---|
| 2013/0197548 | A1* | 8/2013 | Keller | A61F 9/00754 606/166 |
| 2017/0000646 | A1* | 1/2017 | Moon | A61F 9/00754 |
| 2018/0036170 | A1 | 2/2018 | Ghannoum et al. | |

FOREIGN PATENT DOCUMENTS

| | | |
|---|---|---|
| KR | 10-1649105 | 8/2016 |
| KR | 10-1863883 | 6/2018 |

OTHER PUBLICATIONS

Written Opinion of the International Searching Authority for PCT/KR2019/010725 dated Nov. 28, 2019 and its English translation by Google Translate (now published as WO2020/040580).

* cited by examiner

FIG. 13
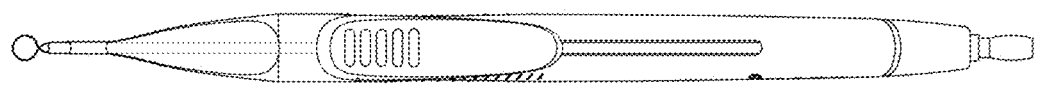
(a)
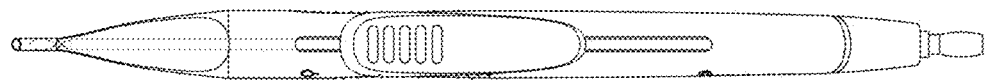
(b)
(c)

FIG. 15
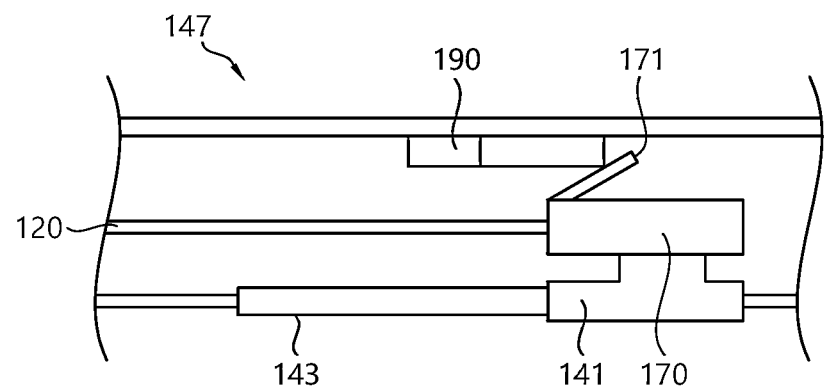
(a)
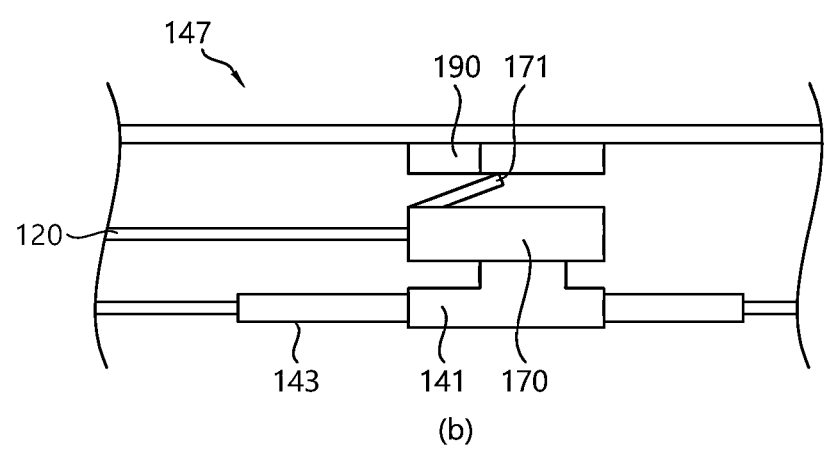
(b)
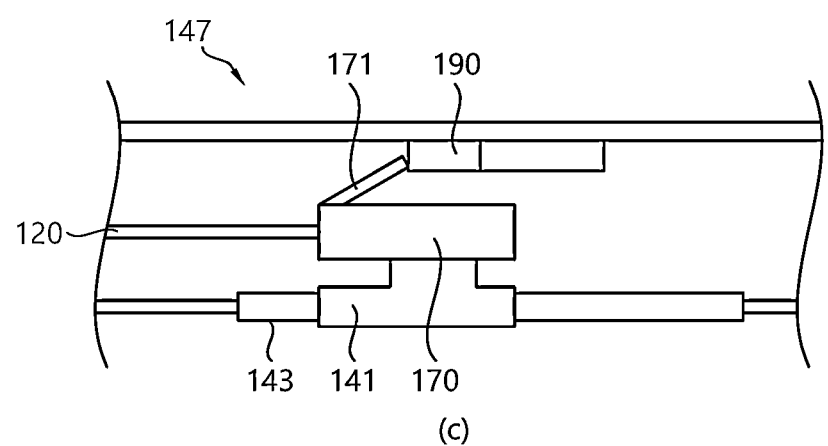
(c)

CAPSULOTOMY DEVICE

CROSS-REFERENCE TO RELATED APPLICATIONS

The present application is the U.S. National Phase of PCT Application No. PCT/KR2019/010725 filed on Aug. 23, 2019, which claims the priority to Korean Patent Application No. 10-2018-0098682 filed on Aug. 23, 2018, the entire contents of which are incorporated herein by reference.

TECHNICAL FIELD

The present disclosure relates to a capsulorhexis device, and more particularly, to a capsulorhexis device which enables accurately and neatly making a circular incision in a anterior surface of a crystalline lens capsule that surrounds a crystalline lens of an eyeball.

BACKGROUND ART

Referring to FIG. 1 illustrating a human eye (1), the human eye (1) is an organ that detects the intensity and wavelength of light to secure a field of vision. The eye (1) consists of a cornea (10), a crystalline lens (20), a crystalline lens capsule (30), an iris (40), a sclera (50), and the like. The cornea (10) is formed to surround the outside of the sclera (50) and is made of a transparent, avascular tissue to refract light, and the crystalline lens (20) is colorless and transparent and serves as a lens of a camera. Also, the iris (40) has pigment therein to determine eye color and serves as an aperture that controls the amount of light entering the eye, and a retina is a part corresponding to a film of the camera and is made of a transparent nervous tissue.

Here, when opacity occurs in the crystalline lens (20), since light is unable to easily pass through the crystalline lens (20) into the eye, an object appears blurred. This is referred to as a cataract. Cataracts may be congenital due to genetic causes or a rubella infection in early pregnancy in some cases, but most cataracts are acquired cataracts which are caused by aging, trauma, systemic diseases, eye inflammation, toxins, and the like. In particular, senile cataracts, which occur as part of aging, are so common that half or more of the elderly in their 60s and most of the elderly over the age of 75 have senile cataracts.

When cataracts occur, prompt treatment is required to prevent vision deterioration. In general, as a method of treating cataracts, a method in which an incision is made in the crystalline lens capsule (30) surrounding the crystalline lens (20) to fragment the crystalline lens (20) located therein by utilizing ultrasound waves and then, simultaneously, the fragmented crystalline lens (20) is removed and an artificial crystalline lens is inserted to substitute therefor is commonly used. That is, an incision with a width of about 2 to 3 mm is made in the cornea (10) using a diamond knife or the like, and an incision tool or the like with a needle having a bent end is inserted through the incision area to scrape off a front surface of the crystalline lens capsule (30) and remove it in a predetermined shape. A method in which the crystalline lens (20), which is exposed due to the removal of the crystalline lens capsule, is fragmented using ultrasound waves, the fragmented crystalline lens (20) is suctioned and discharged to the outside, and an artificial crystalline lens is inserted into and fixed at a position where the crystalline lens (20) was present is mostly used.

However, with regards to a conventional incision tool such as that disclosed in U.S. Pat. No. 4,481,948, since an operator has to insert a needle through an incision area and perform scraping multiple times on the crystalline lens capsule (30) in order to make an incision in an anterior capsule which is a front surface of the crystalline lens capsule (30), there is a limitation in neatly and accurately making a circular incision of an appropriate size in the crystalline lens capsule (30) by utilizing such a conventional incision tool.

In a case in which the size and circularity of an incision site are not constant, side effects may occur due to luxation or atrophy of the crystalline lens, and this may adversely affect the prognosis of vision.

Further, since the incision tool has to be very carefully moved multiple times in order to remove the front surface of the crystalline lens capsule (30) while not causing damage to the cornea or iris that is adjacent to the incision area, there are disadvantages in that the surgery is difficult, the quality of the surgery depends greatly on the skill of the operator, and it takes a long time.

Therefore, in recent years, in the medical industry for cataract treatment, there has been significantly increasing demand for a new type of capsulorhexis device capable of accurately, neatly, and promptly making a circular incision in a front surface of a crystalline lens capsule that surrounds a crystalline lens of an eyeball.

Accordingly, there is a need for a capsulorhexis device capable of easily making an incision within a short time while maintaining the size and circularity of an incision site constant without causing damage to surrounding tissues.

Meanwhile, devices having a structure in which a connecting part of an insertion sleeve and a loop is bent may be considered for a reason in that a direction of insertion through an incision site of the cornea and the central axis of the crystalline lens form a certain angle. However, such a bending structure makes it difficult for an operator to insert the loop into a target position and control the loop.

DISCLOSURE

Technical Problem

The present disclosure is directed to providing a capsulorhexis device capable of safely storing an incision loop without a separate storage cap and improving use convenience and incision quality.

The present disclosure is also directed to providing a capsulorhexis device allowing a perfectly-circular incision to be neatly made in an anterior capsule.

The present disclosure is also directed to providing a capsulorhexis device capable of addressing a problem in that, as a loop stored in a housing passes through a narrow insertion guide for incision surgery, torsional deformation occurs and circularity of a single plane is not maintained, thereby allowing a perfectly-circular incision to be neatly made in a crystalline lens capsule.

The present disclosure is also directed to providing a capsulorhexis device varying a thickness and/or application area of a coating applied to a support part and a curved part of a loop and a moving member coupled to the loop in order to efficiently implement energy transfer and/or energy isolation to and/or from the loop so that, during surgery, an incision is efficiently made in a crystalline lens capsule while not causing damage to surrounding tissues such as the cornea.

The present disclosure is also directed to providing a structure capable of preventing unintentional movement of a loop to safely store the loop in a housing and preventing reuse of a loop that is used one time.

Objectives of the present disclosure are not limited to those mentioned above, and other unmentioned objectives should be clearly understood by those of ordinary skill in the art from the description below.

Technical Solution

One aspect of the present disclosure provides a capsulorhexis device inserted into an incision site of a cornea to make an incision in a crystalline lens capsule surrounding a crystalline lens, the capsulorhexis device including a loop (110) having elasticity and conductivity, a moving member (120) having one end fixed and coupled to the loop (110), a nozzle-type insertion guide (131) configured so that, while an incision is being made in the crystalline lens capsule, a front end thereof is inserted into the incision site of the cornea, and a housing having one end coupled to a rear end of the insertion guide (131), wherein the loop (110) is stored in the housing and, to make the incision in the crystalline lens capsule, slides in the housing together with the moving member to pass through the insertion guide (131) and be unfolded into an anterior chamber of the eye.

The loop (110) may consist of a support part having one end coupled to the moving member and a curved part extending from the other end of the support part to form the loop (110) in a circular shape, and the loop (110) may be stored in the housing without being deformed due to an external force, may be deformed while passing through the insertion guide (131) to make the incision in the crystalline lens capsule, and then may be unfolded and restored to the circular shape after passing through the insertion guide (131).

The loop (110) may be configured to be located on the same virtual plane as the moving member when stored in the housing, at least a portion of the loop (110) may deviate from the plane while the loop (110) slides together with the moving member and passes through the insertion guide (131), and the loop (110) may be unfolded in a circular shape and located on the plane after passing through the insertion guide (131). The moving member may be configured to linearly move on the same plane in a process in which the loop (110) is stored and slides.

The plane may be parallel to an outer upper surface of the insertion guide (131), and the moving member may be configured to slide along the central axis of the insertion guide (131) which has a tubular shape.

The curved part of the loop (110) may be marked with a marker to assist an operator in finding the center of the loop (110).

The outer upper surface of the insertion guide (131) may be formed to be parallel to the plane on which the moving member is disposed, and an internal cavity of the insertion guide (131) may be formed to be long and have a vertically symmetrical cross-section. The central axis connecting the left and right sides of the vertically symmetrical cross-section may be formed to be inclined at a predetermined angle with respect to the plane, and the loop (110) may be deformed as the loop (110) moves along an inner wall of the internal cavity while passing through the internal cavity.

A pair of guide channels (133) formed in a direction in which the loop (110) slides may be provided inside the housing, and the pair of guide channels (133) may consist of a first guide channel (133a) configured to allow one area of the loop (110) to slide while being pressed downward and a second guide channel (133b) configured to allow another area of the loop (110) to slide while being supported upward.

According to another aspect of the present disclosure, the insertion guide (131) may be formed in a long tubular shape having a vertically symmetrical cross-section, and the internal cavity of the insertion guide (131) may be formed to be symmetrical about an axis along which the loop (110) slides and formed to have a slope at a predetermined angle with respect to the plane.

According to one aspect of the present disclosure, the capsulorhexis device may further include a body (140) that is coupled to the other end portion of the housing and has a sliding button (141) provided to slide the loop (110) and the moving member (120). A holder (170) on which the moving member is mounted and which is coupled to the sliding button may be installed in the body (140), and the other end of the moving member may be fixed and coupled to the holder (170) and linearly slide together with the holder (170) due to the sliding button. Also, a guide rail configured to guide linear movement of the holder (170) may be formed inside the body to more precisely guide the linear movement of the moving member.

A protruding part (190) may be formed on an inner wall of the body, a leaf spring (171) may be provided at the holder (170), and when the loop (110) is stored in the housing, the leaf spring (171) may be disposed at a rear end of or behind the protruding part (190) to prevent unintentional sliding of the moving member and allow the loop (110) to be stored while the circular shape thereof is maintained When the sliding button coupled to the holder (170), to which the moving member is fixed, is moved with a predetermined force or more, the leaf spring (171) may move along one surface of the protruding part (190), and after a rear end of the leaf spring (171) is caught at a front end of the protruding part (190), rearward movement of the moving member and the holder (170) may be prevented.

The loop (110) may consist of a rope part (111) in which a plurality of conductive wires are formed to be twisted in the shape of a straw rope to have elasticity and an insulating coating part (112) configured to coat at least one area of the rope part (111). A thickness of the coating part (112) of the loop (110) may be less than or equal to a thickness of a coating part (122) of the moving member (120).

The loop (110) may consist of a support part having one end coupled to the moving member (120) and a curved part coupled to the other end of the support part, and an axis along which the moving member slides may be the same as the central axis of the insertion guide (131).

Another aspect of the present disclosure provides a capsulorhexis device (100) including a loop (110) having elasticity and conductivity, a moving member (120) having one end fixed and coupled to the loop (110), a head part (130) including a housing configured to store the loop (110) therein and an insertion guide (131) coupled to one end portion of the housing to communicate therewith, and a body (140) that is coupled to the other end portion of the housing and has a sliding button (141) provided to slide the loop (110) and the moving member (120) through the head part (130).

In order to make an incision in an anterior capsule, a front end of the insertion guide (131) may be configured to be inserted through an incision site of a cornea, the head part may provide a path along which the loop (110) is moved to the outside through the insertion guide (131), and the loop (110) may slide to pass through the insertion guide (131) from the housing, may be unfolded into an anterior chamber of the eye that is below the cornea, and may be configured to, using high-frequency power supplied thereto, make a circular incision in a site of the anterior capsule that comes in contact with the loop (110).

The loop (110) may consist of a support part having one end coupled to the moving member and a curved part extending from the other end of the support part to form the loop (110) in a circular shape, and the loop (110) may be stored in the housing without being deformed due to an external force, may be deformed while passing through the insertion guide (131) to make an incision in the anterior capsule, and then may be unfolded and restored to the circular shape after passing through the insertion guide (131).

Still another aspect of the present disclosure provides a device inserted into an incision site of a cornea to make an incision in a crystalline lens capsule surrounding a crystalline lens, the device including a loop (110) inserted into the incision site of the cornea to make a circular incision in the crystalline lens capsule located below the cornea, a head part that is configured to store the loop (110) therein and has an insertion guide (131) provided at one side to provide a path along which the loop (110) is moved to the outside through the insertion guide (131) while an incision is being made in an anterior capsule, and a body having a sliding button provided in at least a partial area of an outer surface so as to slide the loop (110) and a moving member, to which one end of the loop (110) is fixed and coupled, through the head part, wherein the loop (110) has an elliptical shape when disposed in a housing of the head part prior to passing through the insertion guide (131) and moving to the outside, and the elliptical shape is an elliptical shape in which a diameter in a direction perpendicular to a direction in which the loop (110) slides is larger than a diameter in the direction in which the loop (110) slides.

Also, more preferably, the loop (110) may consist of a rope part in which a plurality of wires are formed to be twisted in the shape of a straw rope to have elasticity and a coating part configured to coat at least one area of the rope part.

Also, more preferably, a thickness of the coating part of the loop (110) may be less than or equal to a thickness of a coating part of the moving member.

Also, more preferably, a pair of guide channels formed in a direction in which the loop (110) slides may be provided inside the head part.

Also, more preferably, the pair of guide channels may consist of a first guide channel configured to allow one area of the loop (110) to slide while being pressed downward and a second guide channel configured to allow another area of the loop (110) to slide while being supported upward.

Also, more preferably, the loop (110) may consist of a support part having one end coupled to the moving member and a curved part coupled to the other end of the support part, and the coating part may be applied to the entire circumference of the support part and to a circumference of each of a left side, a right side, and an upper side of the curved part.

Advantageous Effects

According to a capsulorhexis device according to an embodiment of the present disclosure, safety, use convenience, and incision quality when making an incision in a crystalline lens capsule are excellent.

Also, storage convenience and safety are improved in the capsulorhexis device according to the present disclosure.

Also, according to a capsulorhexis device according to an embodiment of the present disclosure, since a pair of guide channels are disposed in one area of a head part along which a loop slides, a problem in that one side of the loop is twisted and deformed can be prevented, and accordingly, the loop is allowed to, after passing through an insertion guide, be restored to a perfectly-circular shape within a single plane without torsional deformation, and thus a perfectly-circular incision can be neatly made in a crystalline lens capsule.

Also, according to a capsulorhexis device according to an embodiment of the present disclosure, by varying a thickness and/or application area of a coating applied to a support part and a curved part of a loop and a moving member coupled to the loop, energy transfer and/or energy isolation to and/or from the loop can be efficiently implemented.

According to still another embodiment of the present disclosure, since an operator can easily unfold a loop at a desired position and find the center of the loop when making an incision in a crystalline lens capsule, the convenience and quality of an operation can be improved.

DESCRIPTION OF DRAWINGS

In order to provide better understanding of the drawings referenced in the detailed description of the present disclosure, brief description of each drawing is provided.

FIG. 13 is a conceptual diagram illustrating movement of the loop (110) and a change in the shape of the loop (110) due to the movement thereof according to an embodiment of the present disclosure.

FIG. 15 is a conceptual diagram illustrating configurations of a cover (147) constituting the body (140), a holder (170) to which a protruding part (190) and a moving member are fixed and coupled, a slot (143), and a sliding button (141) and changes in the shapes thereof due to sliding according to an embodiment of the present disclosure.

MODES OF THE INVENTION

Figure 1:
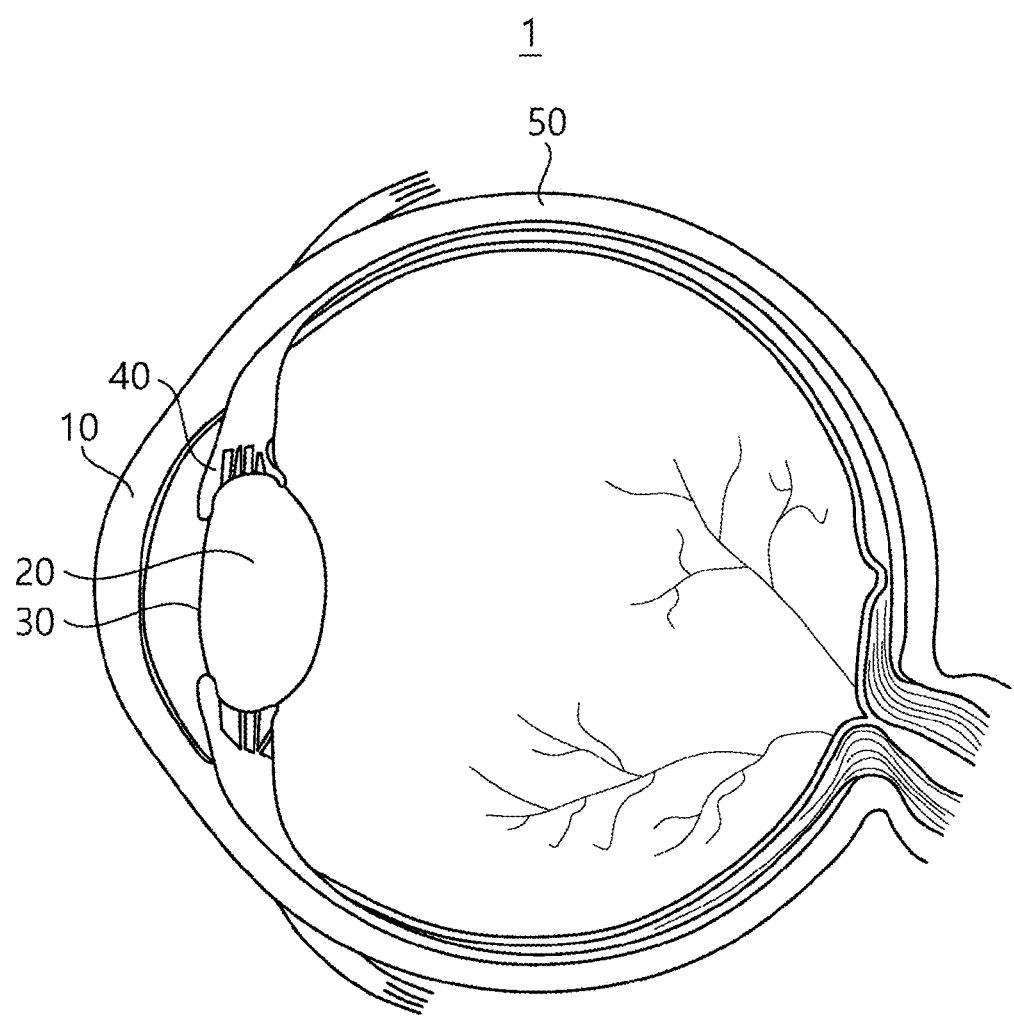
FIG. 1 schematically illustrates a structure of an eye (1).

Hereinafter, embodiments according to the present disclosure will be described with reference to the accompanying drawings. In assigning reference numerals to elements in each drawing, it should be noted that like reference numerals are assigned to like elements as much as possible even when the elements are illustrated in different drawings. Also, in describing the embodiments of the present disclosure, when detailed description of a known related art or function is deemed to hinder the understanding of the embodiments of the present disclosure, the detailed description thereof will be omitted. In addition, although the embodiments of the present disclosure will be described below, the technical idea of the present disclosure is not limited thereto, and the embodiments may be modified by those of ordinary skill in the art and embodied in various other ways.

Throughout the specification, when a certain part is described as being "connected" to another part, this not only includes a case in which the certain part is "directly connected" to the other part but also includes a case in which the certain part is "indirectly connected" to the other part while another element is present therebetween. Throughout the specification, when a certain part is described as "including" a certain element, unless particularly stated otherwise, this indicates that the certain part may further include another element instead of excluding another element. In addition, in describing elements of the embodiments of the present disclosure, terms such as first, second, A, B, (a), and (b) may be used. Such terms are only used to distinguish one element from another element, and the essence, order, sequence, or the like of the corresponding element is not limited by the terms.

Figure 2:
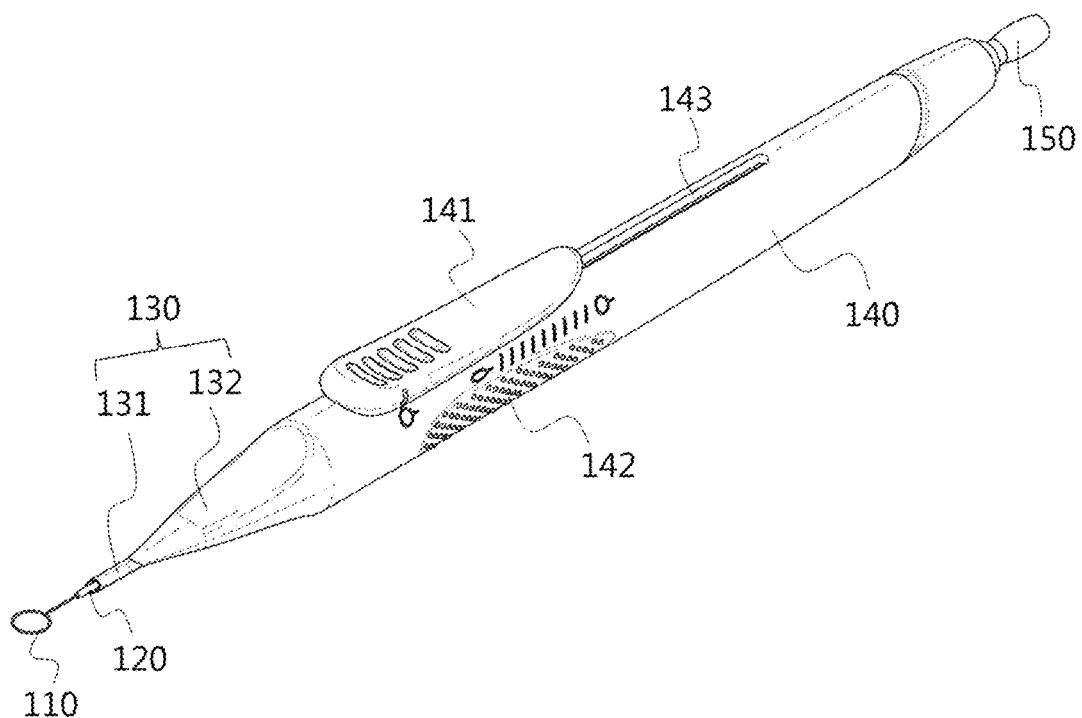
FIG. 2 is a schematic perspective view of an anterior capsule incision device (100) according to an embodiment of the present disclosure.

FIG. 2 is a schematic perspective view of a capsulorhexis device 100 according to an embodiment of the present disclosure.

Referring to FIG. 2, the capsulorhexis device 100 according to an embodiment of the present disclosure is a device inserted into an incision site of a cornea 10 to make an incision in a crystalline lens capsule 30 surrounding a crystalline lens 20. The capsulorhexis device 100 may have the shape of a pen as a whole to be easily gripped by a user and to facilitate surgery. The capsulorhexis device 100 may include, as its elements, a loop 110, a moving member 120, a head part 130, a body 140, and a power connection part 150.

Meanwhile, in FIGS. 2 to 15, although the moving member 120 is illustrated as having a larger diameter than the loop 110, this is due to being drawn with exaggeration to show a coupling configuration with a support part, and particularly the moving member has a very small diameter as compared to an insertion guide 131 of the head part.

The loop 110 having elasticity and conductivity may be configured to be inserted into the incision site of the cornea 10 to make a circular incision in the crystalline lens capsule 30 located below the cornea 10. While an incision is being made in the crystalline lens capsule, the loop 110 may pass through the insertion guide 131 and be exposed to the outside together with a partial area of the moving member 120, and the state in which the loop 110 is exposed is exemplarily illustrated in FIG. 2. When a high frequency supplied through the power connection part 150 is applied to the loop 110, energy is transferred to an electrolyte of the crystalline lens capsule 30 coming in contact with the loop 110, and heat and/or plasma are/is generated. Since this process causes the tissue of the anterior capsule to be heated or degenerated, the circular incision may be made within a short time.

The power connection part 150 illustrated in FIG. 2 may be implemented as a terminal type or a cable type. Although not disclosed in detail in the drawing, the power connection part is electrically connected to the moving member 120, which is made of a conductor, using a cable or a terminal, and high-frequency power is transmitted to the conductive loop 110 connected to the moving member.

The loop 110 consists of the support part and a curved part coupled to one end of the support part, portions of the loop 110 are disposed to be spaced apart at a predetermined interval in a coupling area between the support part and the curved part, and the other end of the support part of the loop 110 is fixed and coupled to the moving member 120. The loop 110 and the moving member 120 may slide together due to manipulation of a sliding button 141 which is able to slide back and forth along a slot 143. A structure for the sliding is disclosed in FIGS. 14 and 15 and will be described below.

The head part 130 consists of the insertion guide 131 through which the loop 110 passes to be exposed to the outside while an incision is being made in the crystalline lens capsule and a housing 132 which has one end coupled to the insertion guide 131 and the other end coupled to one end of the body 140. The head part 130 may store the loop 110 therein and provide a path along which the loop 110 is moved to the outside through the insertion guide 131 while an incision is being made in the crystalline lens capsule 30. For reference, the head part 130 may be implemented using a transparent or translucent material, and accordingly, the operator may easily check by visual inspection the movement of the loop 110 and a change in the shape of the loop 110 due to the movement.

FIG. 13 exemplarily illustrates the movement of the loop 110 through the head part 130, which is implemented using a transparent or translucent material, and a change in the shape of the loop 110 due to the movement. The loop 110 is configured to be stored in the housing as in FIG. 13C, configured to slide in the housing together with the moving member and pass through the insertion guide 131 as in FIG. 13B to make an incision in the crystalline lens capsule, and configured to be unfolded into an anterior chamber of the eye as in FIG. 13A.

According to an embodiment of the present disclosure, a predetermined indication mark may be further formed on one side surface of the body 140, more specifically, a space between the sliding button 141 and an anti-slip protrusion 142, and the indication mark may be implemented in an area corresponding to a position of the sliding button 141 for each of the case in which the loop 110 is exposed to the outside (refer to FIG. 13A), the case in which the loop 110 is disposed in the insertion guide 131 (refer to FIG. 13B), and the case in which the loop 110 is stored in the housing 132 (refer to FIG. 13C).

The sliding button 141 which slides the loop 110 and the moving member 120, which is fixed and coupled to the loop 110, through the head part 130 may be disposed in at least a partial area of an outer surface of the body 140, more preferably, in a longitudinal direction of the slot 143. More specifically, since one end of the moving member 120 is coupled to one end of the support part of the loop 110 and the other end of the moving member 120 is directly/indirectly coupled to a lower end surface of the sliding button 141, the operator may move the sliding button 141 back and forth along the slot 143 to simultaneously move the loop 110 and the moving member 120 back and forth, and in particular, in a case in which the sliding button 141 moves forward (that is, the user pushes the sliding button 141 toward the head part) to make an incision in the crystalline lens capsule 30, the loop 110 may be completely exposed to the outside as exemplarily illustrated in FIG. 2.

For reference, in one area of the sliding button 141 provided in the body 140, for example, a plurality of grooves (or protrusions) may be formed in an area corresponding to a thumb of the user. Accordingly, when the user moves the sliding button 141 back and forth, not only the movement of the sliding button 141 is facilitated, but also slipping of the user's fingers may be prevented. In addition, the anti-slip protrusion 142 may be further provided on one side surface or both side surfaces of the body 140 and may not only prevent slipperiness that may occur in a case in which the user grips the body 140 of the capsulorhexis device 100 to perform capsulorhexis but also further improve convenience in management and handling of the product by the user.

Here, as illustrated in FIG. 2, the loop 110 that is exposed to the outside after passing through the insertion guide 131 may have a perfectly-circular shape.

Figure 3:
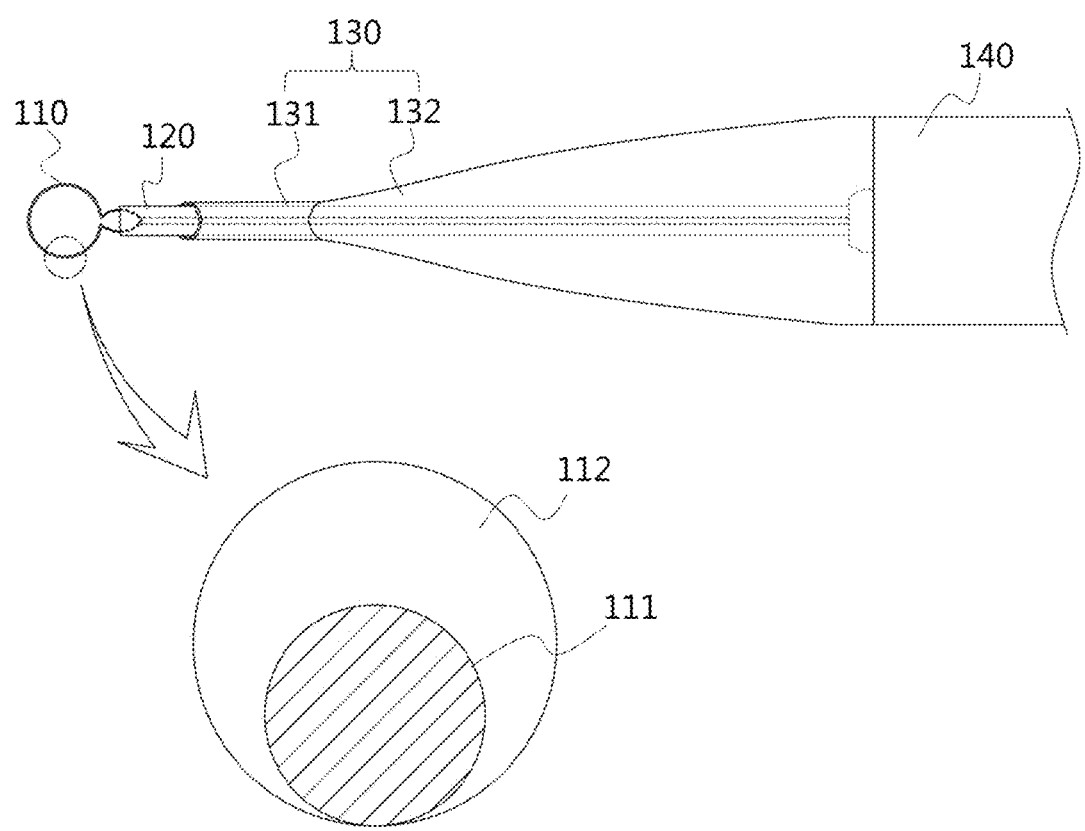
FIG. 3 is a partial enlarged view of a capsulorhexis device and a cross-section of a curved part of a loop (110) of the device according to an embodiment of the present disclosure.

FIG. 3 illustrates a state in which the loop 110 is unfolded to the outside of the insertion guide 131 in the capsulorhexis device according to an embodiment of the present disclosure and includes an enlarged view of a longitudinal cross-section of the curved part of the loop 110.

The loop 110 according to an embodiment of the present disclosure may consist of a rope part 111 and a coating part 112. The rope part 111 may have a plurality of wires (not illustrated) formed to be twisted in the shape of a straw rope to have elasticity, and the coating part 112 may coat at least one area of the rope part 111. For example, the rope part may have a 1×7 rope structure which is formed by twisting seven wires in the form of straw rope, and a portion of an outer surface of the rope part may be coated with an insulating material.

The process of using the capsulorhexis device 100 according to an embodiment of the present disclosure to make a circular incision in the crystalline lens capsule 30 will be described as follows.

First, the operator forms an incision site in the cornea 10 using an incision tool and inserts one end of the insertion guide 131 into the incision site. Here, a front end of the insertion guide 131 being inserted may have an inclined part to facilitate the insertion of the insertion guide 131 through the incision site of the cornea. That is, a distal end of the insertion guide 131 formed in the shape of an elliptical tube may have a shape that is obliquely inclined from top to bottom.

When the operator moves the sliding button 141 forward in a state in which at least a portion of the insertion guide 131 is inserted, the loop 110 is exposed to the outside of the head part 130 through the insertion guide 131 and is placed on an upper portion of the crystalline lens capsule 30 where an incision will be made.

In the state in which the loop 110 is placed on the upper portion of the crystalline lens capsule 30, when a power switch is turned on and the loop 110 generates heat using a high frequency, the loop 110, more specifically, the curved part of the loop 110 generates bubbles on the tissue of the crystalline lens capsule 30 and then generates a plasma through ionization to promptly make a circular incision in the anterior capsule. When the operator moves the sliding button 141 rearward after the circular incision is made in the crystalline lens capsule 30, the loop 110 is inserted into the insertion guide 131, and thus the capsulorhexis device may be withdrawn through the incision site afterwards. In this way, using the device of the present disclosure, the operator may promptly and accurately make a circular incision in the crystalline lens capsule 30 where the incision is desired to be made.

That is, since a circular incision may be accurately made in the front surface of the crystalline lens capsule 30 surrounding the crystalline lens 20, revision surgery due to a surgical failure may be prevented and the surgery may be safely and easily performed. Also, since the loop 110 making an incision in the crystalline lens capsule 30 is formed by twisting the plurality of wires in the shape of a straw rope, deformation of the loop 110 due to heat may be prevented.

In addition, since the loop 110 generates heat using a high frequency to make an incision in the crystalline lens capsule 30, deformation of the loop 110 due to generating heat by itself may be prevented, and since a heating time using heat is shortened, an operating time of the operator may be further reduced.

Figure 4:
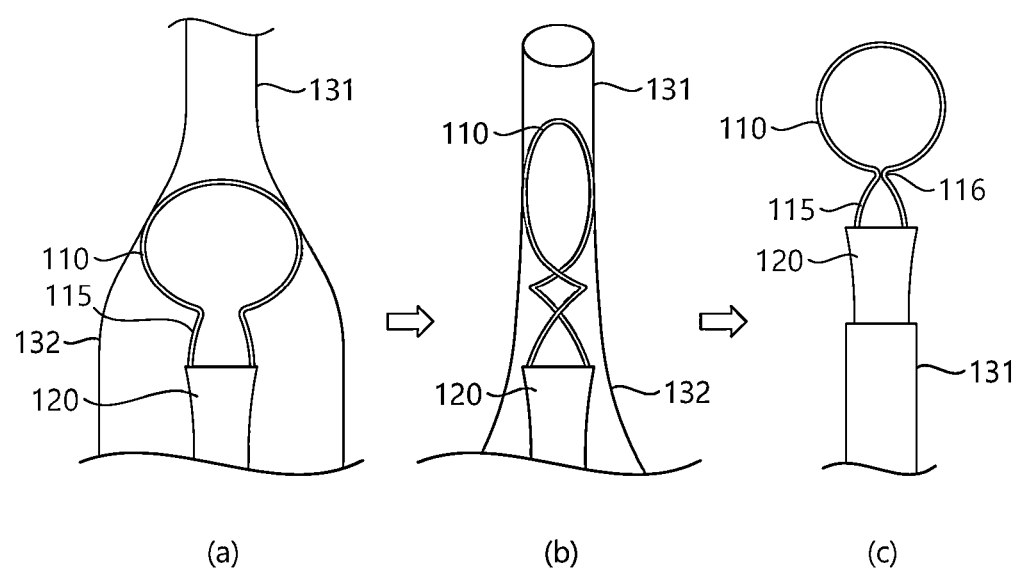
FIG. 4 is a conceptual diagram for describing changes in the shape of the loop (110) before, while, and after the loop (110) passes through an insertion guide (131) according to an embodiment of the present disclosure.

FIG. 4 is a conceptual diagram for describing changes in the shape of the loop 110 before and after the loop 110 passes through the insertion guide 131 according to an embodiment of the present disclosure. For reference, through numerous tests and a large amount of research and development on crystalline lens capsule incisions, the inventors of the present disclosure have found that: (i) in making an incision in the front surface of the crystalline lens capsule 30, when the incision area is implemented in a perfectly-circular shape, the effect of cataract surgery may be maximized; and (ii) when the loop 110 passes through the insertion guide 131 to be exposed to the outside to make an incision in the crystalline lens capsule 30, predetermined deformation occurs in the loop 110.

FIG. 4A illustrates the shape of the loop 110 when the loop 110 is stored in the housing 132 before passing through the insertion guide 131, FIG. 4B illustrates the shape of the loop 110 while the loop 110 passes through the insertion guide 131 (here, the loop 110 moves inside the insertion guide 131 while portions of the loop 110 cross each other), and FIG. 4C illustrates the shape of the loop 110 after the loop 110 passes through the insertion guide 131 and is exposed to the outside of the head part 130.

As illustrated in FIG. 4, while the loop 110 passes through the insertion guide 131, the transverse dimension (which is in a direction perpendicular to the sliding direction (hereinafter, the direction will be referred to as "transverse direction")) of the loop 10 decreases, and the extent of the decrease increases as an inner diameter of the insertion guide 131 is smaller. A diameter of the loop 110 in the direction in which the loop 110 slides (hereinafter, the direction will be referred to as "longitudinal direction") is substantially the same before and after the loop 110 passes through the insertion guide 131.

The loop 110 may be implemented to have an elliptical shape when the loop 110 is disposed in the housing 132 of the head part 130 prior to passing through the insertion guide 131 to move to the outside. Here, the elliptical shape of the loop 110 may be an elliptical shape in which a diameter A in the direction perpendicular to the direction in which the loop 110 slides is larger than a diameter B in the direction in which the loop 110 slides (that is, A>B).

The extent to which the loop 110 is longer in the transverse direction than in the longitudinal direction may be determined according to specifications of the rope of the loop 110, a thickness of the loop 110, a material of the loop 110, a length of the loop 110, a usage history of the loop 110, the inner diameter of the insertion guide 131, and the like.

In addition, as clearly illustrated in FIG. 4, it can be seen that a width of a neck portion of the loop 110 (that is, a portion 116 thereof where the support part and the curved part are combined) also decreases after the loop 110 passes through the insertion guide 131. In making an incision in the front surface of the crystalline lens capsule 30, when the width of the neck portion of the loop 110 after the loop 110 passes through the insertion guide 131 is implemented to have a predetermined size, e.g., less than or equal to 0.7 mm, making a perfectly-circular incision becomes possible even when the neck portion of the loop 110 has a certain width.

Meanwhile, for the loop 110 to make a perfectly-circular incision in the front surface of the crystalline lens capsule 30, it is very important that the loop 110 is arranged in a straight line, that is, has a high flatness, when viewed from the side. Preferably, the loop 110 elastically restored after passing through the insertion guide 131 may have a perfect circular shape on a single plane to facilitate making the perfectly-circular incision, and more preferably, the loop 110 may be disposed to be coplanar with the moving member.

However, since the diameter of the loop 110 is much larger than the inner diameter of the insertion guide 131 as illustrated in FIGS. 4B and 13B, the loop 110 moves inside the insertion guide 131 while portions of the loop 110 cross each other. Of particular concern is torsional deformation.

In a case in which torsional deformation occurs throughout the loop 110 and the deformation is relatively uniformly distributed, the loop 110 made of an elastic material may easily be restored to the circular shape disposed on the single plane after passing through the insertion guide 131. However, in a case in which torsional deformation is focused on one portion of the loop 110, the loop 110 may not be restored to its original state from a partially or entirely twisted state even after the loop 110 passes through the insertion guide 131. Such a phenomenon may be more prominent in the case of the loop 110 including the rope part 111 formed by twisting the plurality of wires in the shape of a straw rope. A partial area of the loop 110 is deformed and irregularly twisted as the loop 110 passes through the narrow insertion guide 131 along the direction in which the plurality of wires are twisted (for example, clockwise, counterclockwise, and the like), and the loop 110 is not restored to its original state even after the loop 110 passes through the insertion guide 131.

Figure 5:
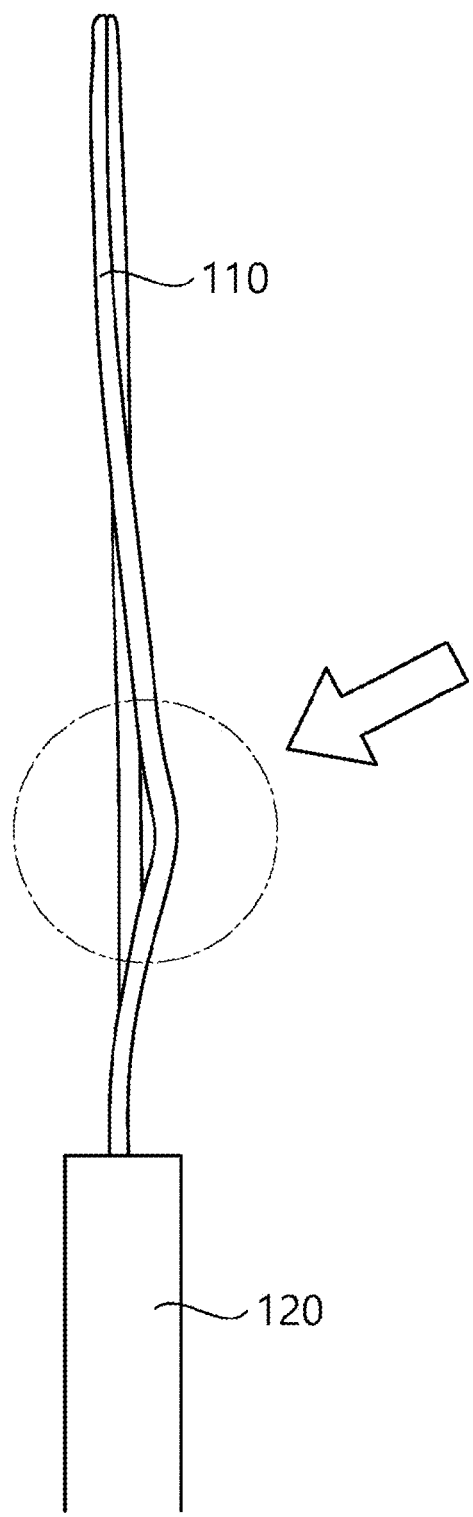
FIG. 5 is an exemplary lateral view for describing torsional deformation of the loop (110) according to an embodiment of the present disclosure.
Figure 6:
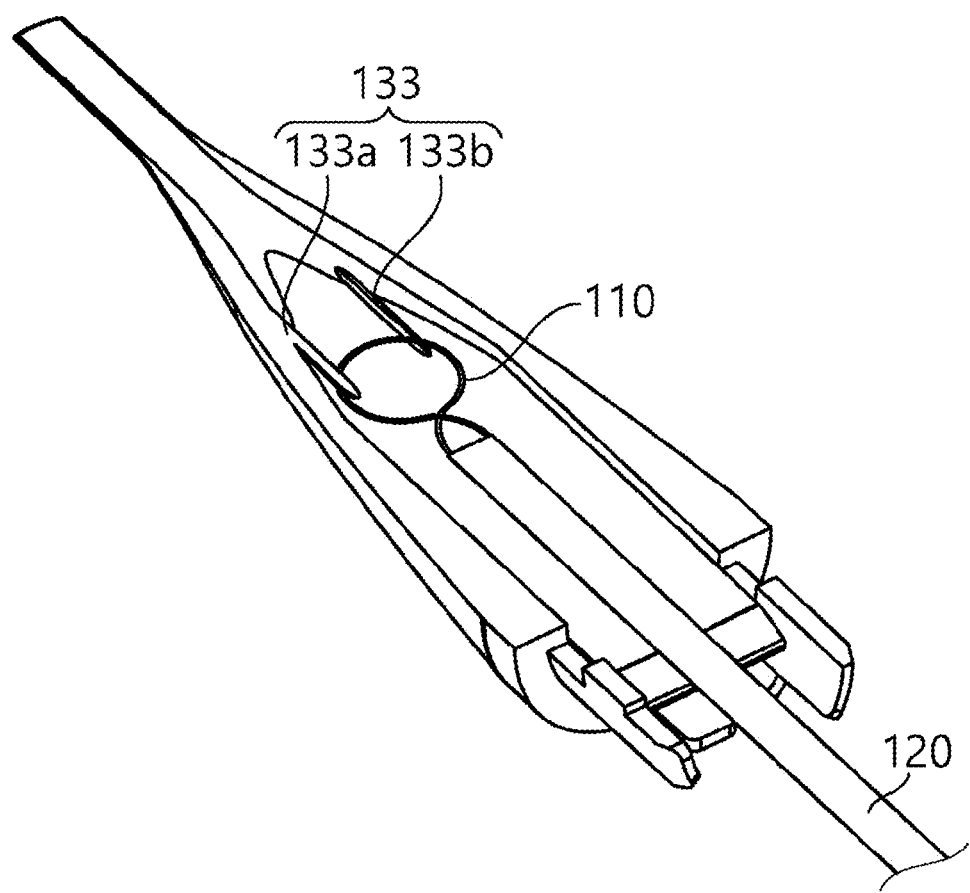
FIG. 6 is a cross-sectional view of a head part (130) including a pair of guide channels (133) for controlling the torsional deformation of the loop (110) illustrated in FIG. 5.

FIG. 5 is an exemplary lateral view for describing torsional deformation of the loop 110 according to an embodiment of the present disclosure, and FIG. 6 illustrates a cross-sectional view of the head part 130 including a pair of guide channels 133 to control the torsional deformation of the loop 110 illustrated in FIG. 5 to prevent permanent deformation thereof.

As illustrated in FIG. 5, when the loop 110 is not completely flat and one area of the loop 110 is twisted and deformed, this serves as a factor that hinders making an accurate incision in the crystalline lens capsule 30 during surgery to make an incision in the crystalline lens capsule. For example, when deformation is focused on the left side of the loop 110 and the left side of the loop 110 is slightly lifted, a problem may occur in that an incision is first made by the right side of the loop 110 that comes in contact with the crystalline lens capsule 30 first while an incision is being made in the crystalline lens capsule 30, and this may result in an inaccurate crystalline lens capsule incision.

A configuration of the head part 130 for controlling the torsional deformation of the loop 110 to be distributed is exemplarily illustrated in FIG. 6. As described above with reference to FIG. 4, in the case in which the loop 110 moves inside the insertion guide 131, portions of the loop 110 cross each other, and here, the pair of guide channels 133 configured to control torsional deformation that occurs at any one side of the loop 110 may be disposed in a space of the housing 132.

More specifically, as illustrated in FIG. 6, according to an additional embodiment of the present disclosure, the pair of guide channels 133 formed in the direction in which the loop 110 slides may be provided inside the head part 130, and the pair of guide channels 133 may consist of a first guide channel 133a configured to allow one area of the loop 110 to slide while being pressed downward and a second guide channel 133b configured to allow another area of the loop 110 to slide while being supported upward.

Therefore, by allowing one side of the loop 110, which is about to be lifted due to the twisting characteristic of the rope part 111, to move through the first guide channel 133a that allows the one side of the loop 110 to be pressed downward when passing through the head part 130, it is ultimately possible to substantially eliminate torsional deformation that may occur when the loop 110 is exposed to the outside to make an incision in the crystalline lens capsule 30.

For reference, although FIG. 6 exemplarily illustrates a structure in which one area of the loop 110 is pressed by the first guide channel 133a and another area of the loop 110 is supported by the second guide channel 133b, according to another embodiment of the present disclosure, the pair of guide channels 133 may also be implemented in a form in which one area of the loop 110 is supported by the first guide channel 133a and another area of the loop 110 is pressed by the second guide channel 133b. Also, although FIG. 6 exemplarily illustrates the guide channels 133 that consist of the two guide channels 133a and 133b, more or less guide channels may be implemented according to various implementation examples or embodiments.

In relation thereto, in order to prevent a torsional deformation phenomenon due to the plurality of wires being twisted in a specific direction, according to an additional embodiment of the present disclosure, a half area of the rope part 111 may be implemented to be twisted clockwise and the other half area of the rope part 111 may be implemented to be twisted counterclockwise so that the rope part 111 is not twisted in one specific direction as a whole.

Figure 7:
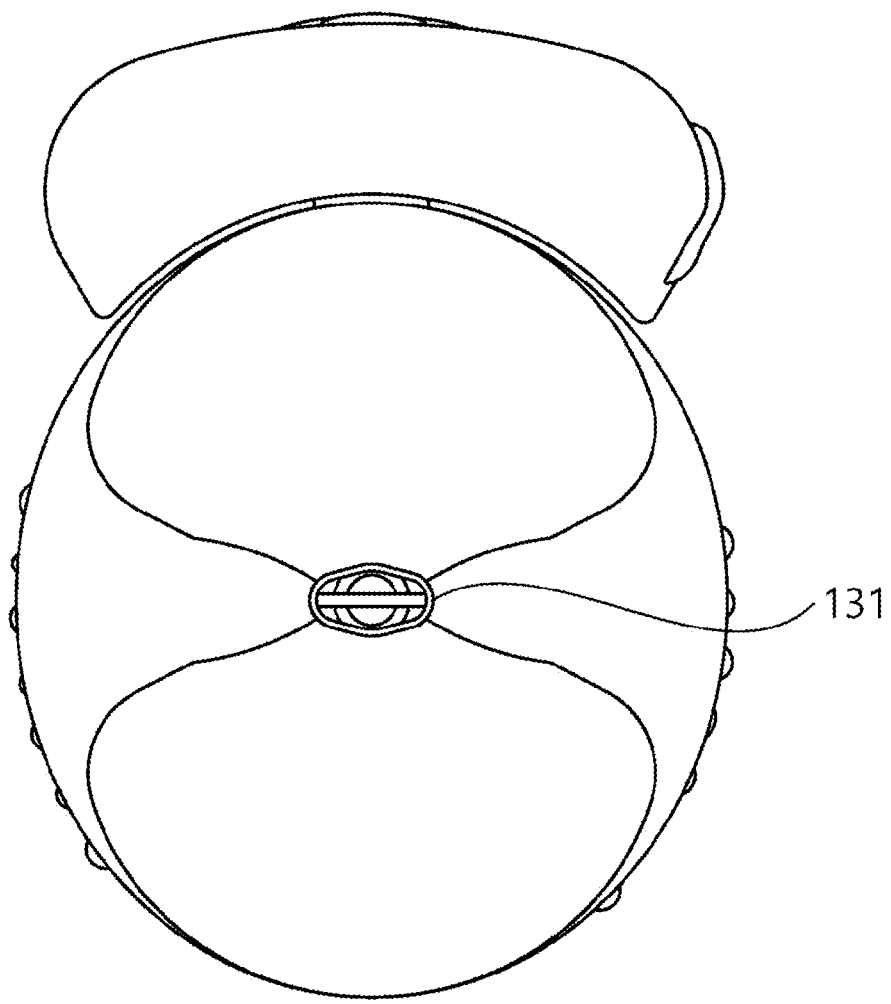
FIG. 7 is a front view of a capsulorhexis device that is viewed from a front end side in a state in which the loop (110) is disposed in the insertion guide (131) according to an embodiment of the present disclosure.

FIG. 7 is a cross-sectional view of the insertion guide 131 according to an embodiment of the present disclosure. Preferably, the insertion guide 131 may be implemented to be as small as possible and optimum as possible according to the shapes and sizes of the loop 110 and the moving member 120 that pass through the insertion guide 131. To this end, in contrast to a general insertion guide 131 that has the shape of a simple track, the insertion guide 131 according to an embodiment of the present disclosure has a cross-sectional shape in which a central portion of a long side of a track is made slightly thicker and, simultaneously, a width of the long side of the track is slightly decreased (a substantially rhombic shape), and consequently, it is possible to implement the insertion guide 131 to be as space-efficient as possible according to the size of a corneal incision knife being used.

Still another embodiment of the present disclosure in which torsional deformation of the loop 110 is controlled to be distributed while the loop 110 passes through the insertion guide 131 and, after the loop 110 passes through the insertion guide 131, the loop 110 is restored to have a circular shape and be coplanar with the moving member 120 will be described with reference to FIGS. 8 to 10.

The moving member 120 is made of a conductive rod that has rigidity, one end of the moving member 120 is coupled to the loop 110, and the other end of the moving member 120 is coupled to a holder 170 installed in the body 140. The loop 110 is stored in the housing 132 without deformation in a state in which the loop 110 does not receive an external force. One end of the loop 110 is pressed and fixed to the moving member 120 made of a conductor, and the loop 110 is laterally supported in the housing by the moving member that has rigidity.

A support part 115 of the elastic loop 110 is pressed and coupled to one end of the moving member 120 by cold forging, and the coupling allows the loop 110 and the moving member 120 to maintain a state of being coupled to each other with a predetermined rigidity or higher and to be coplanar. The moving member is configured to do linear motion on one plane while the moving member being housed in the housing and slidingly moving. A structure therefor will be described below.

The moving member 120 is a cylindrical, quadrilateral, or polygonal rod that has a very small diameter as compared to the insertion guide 131 and is able to linearly slide without being interfered with when passing through the insertion guide 131. Preferably, the moving member 120 may linearly slide on a plane that the loop 110 forms while being stored in the housing and may have a movement path that coincides with the central axis of the insertion guide 131, but the present disclosure is not limited thereto.

The moving member is maintained to be coplanar with the loop 110 even after a distal end of the moving member is exposed to the outside while and after the moving member passes through the insertion guide 131 from the housing 132.

In order to control deformation of the loop 110, which occurs as the loop 110 passes through the insertion guide 131, to be distributed, an internal cavity of the insertion guide 131 is formed so that both sides are asymmetrical to be vertically offset at a predetermined angle with respect to a movement plane of the moving member.

Figure 8:
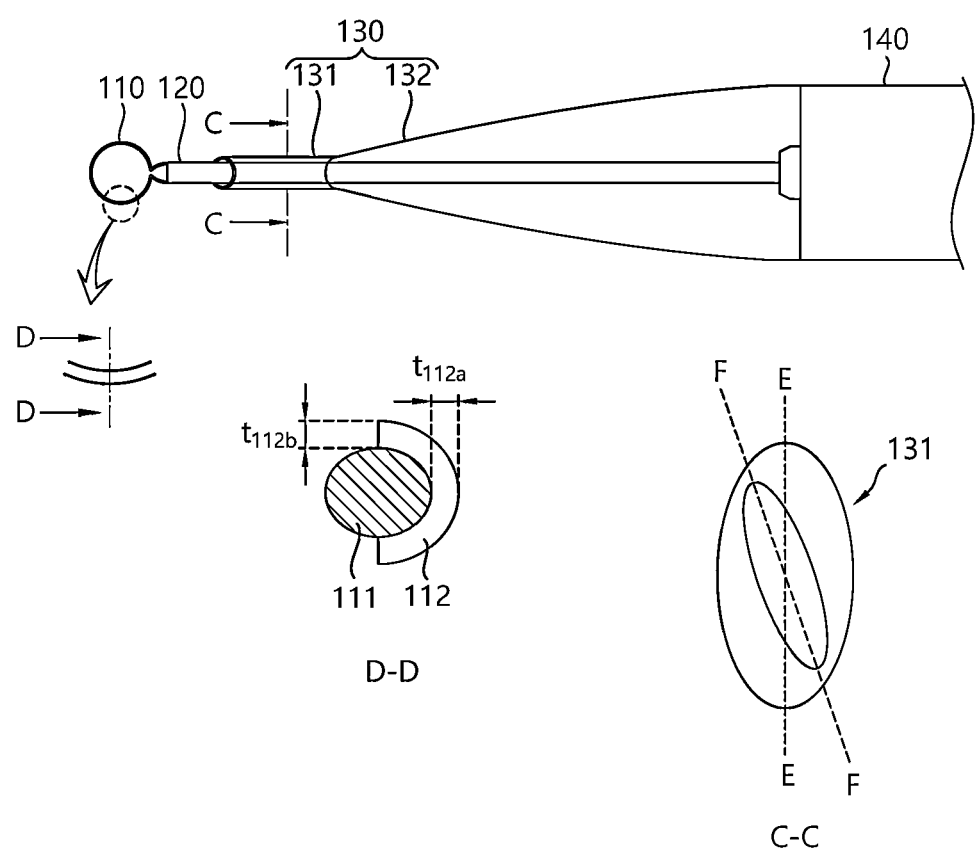
FIG. 8 is a view of a capsulorhexis device illustrating a structure of an insertion guide (131) according to another embodiment of the present disclosure.

C-C of FIG. 8 shows a transverse cross-section of the insertion guide 131 according to an embodiment of the present disclosure. In an embodiment of FIG. 8, the insertion guide is an elliptical tube, and an outer surface of the insertion guide is vertically symmetrical with respect to the movement path of the moving member as the center. On the other hand, the internal cavity along which the moving member and the loop 110 pass is formed as an elliptical tube that is inclined at a predetermined angle with respect to the outer surface of the insertion guide. That is, E-E is simultaneously a long axis of an ellipse, which is an outer shape of the insertion guide 131, and a plane that the moving member 20 and the loop 110 form in the housing. F-F is a long axis of an ellipse, which is a cross-section of the internal cavity of the insertion guide 131, and is formed to be inclined at a predetermined angle with respect to the long axis E-E of the outer ellipse. The shape and arrangement of the internal cavity serve to guide, as the diameter of the loop 110 is decreased as the loop 110 moves along the central axis of the moving member where the two long axes meet, the left and right sides of the loop 110 to vertically cross over each other and the deformation to be symmetrically distributed and maintained.

Due to such a configuration, torsional deformation of the loop 110 is controlled to be distributed in balance to prevent a case in which torsional determination is focused on a specific portion in the cavity of the insertion guide 131 and permanent deformation occurs.

Then, since the loop 110 is unfolded in a circular shape on a single plane including the moving member when the loop 110 exits the insertion guide 131, incision quality may be improved.

Here, the outer shape of the insertion guide 131 and the cross-section of the internal cavity of the insertion guide 131 are not arranged to have the same shape because, when the operator performs surgery, the operator inserts the insertion guide 131 into the incision site of the cornea on the basis of the outer shape, that is, the outer surface, of the insertion guide 131 and adjusts balance. Therefore, preferably, the single plane that the moving member and the loop 110 form may be parallel to an upper surface and/or a lower surface of the insertion guide 131.

However, in order to control torsional deformation of the loop 110, the internal cavity of the insertion guide 131 is formed at a predetermined angle with respect to the single plane and thus formed to be vertically asymmetrical to induce the left and right sides of the loop 110 to move at different heights. The internal cavity of the insertion guide 131 induces controlled crossover and distributed torsional deformation to occur in the loop 110 when the loop 110 passes through the insertion guide 131. That is, the internal cavity of the insertion guide 131 is formed to be long and have a symmetrical cross-section, and the central axis connecting the left and right sides of the symmetrical cross-section is formed to be inclined at a predetermined angle with respect to the plane so that, while the loop 110 passes through the internal cavity, the loop 110 is deformed as the loop 110 moves with a slope along an inner wall of the internal cavity. While the left and right sides of the loop 110 are symmetrical to each other, the left and right sides are offset to be at different heights so that deformation of the loop 110 is distributed in balance.

In other words, the outer upper surface and the outer lower surface of the insertion guide 131 may be formed to be parallel to a horizontal surface, and the internal cavity of the insertion guide 131 may be formed to have a vertically asymmetrical cross-section so that, while the loop 110 passes through the internal cavity, at least a portion of the loop 110 deviates from the plane and is deformed to have a slope. The cross-section may be configured in various shapes such as an elliptical shape and a pressed rectangular shape.

Figure 9:
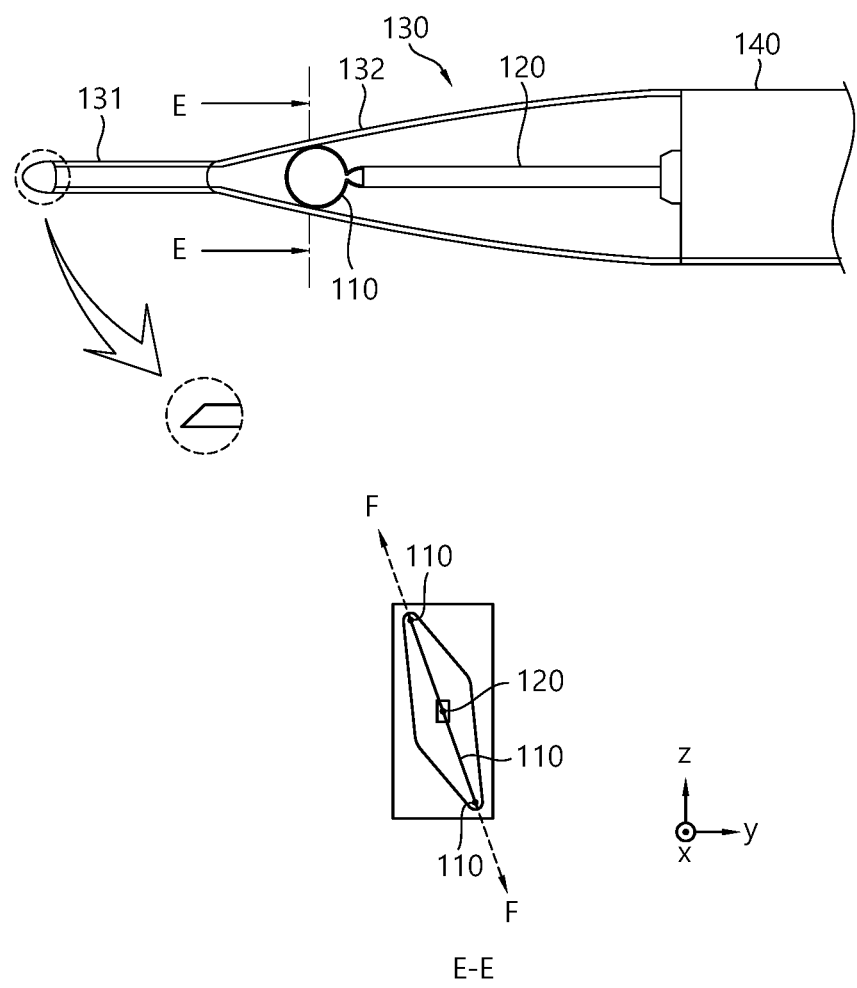
FIG. 9 is a view of a capsulorhexis device illustrating a structure of an insertion guide (131) according to another embodiment of the present disclosure.
Figure 10:
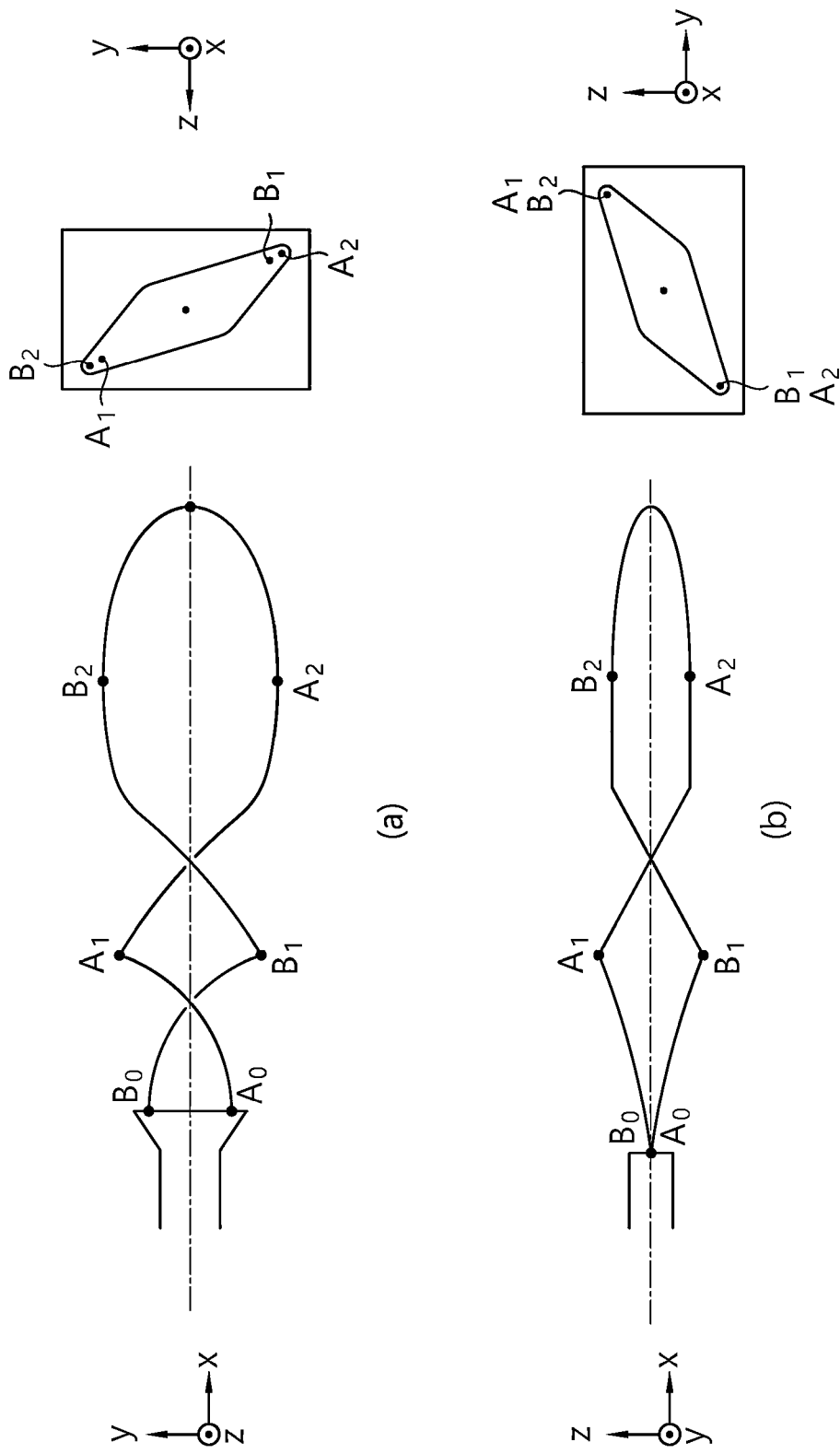
FIG. 10 is a view schematically illustrating ways in which the loop (110) is deformed when the loop (110) passes through the insertion guide (131) according to another embodiment of the present disclosure.

FIG. 10 illustrates crossover deformation of the loop 110, and FIG. 9 includes an enlarged view of the cross-section (taken along line E-E) of the insertion guide 131 having a flat quadrilateral shape. Although there are differences between the cross-sectional shapes of FIGS. 9 and 8, these correspond to variations in design, and the insertion guide 131 may have various other cross-sectional shapes.

In this way, the loop 110 is configured to be coplanar with the moving member 120 when stored in the housing 132, the loop 110 slides together with the moving member 120 and passes through the insertion guide 131, and after the loop 110 passes through the insertion guide 131, the loop 110 is configured to be unfolded and be coplanar with the moving member 120.

Meanwhile, according to yet another embodiment of the present disclosure, an inclined cavity may be, instead of being formed in the insertion guide 131, formed in an area which is disposed at a front surface of the housing and in which a cross-sectional area narrows to be connected to the insertion guide 131. That is, an inclined cavity may be formed to induce the crossover of the loop 110 from a position where the circumference of the loop 110 comes in contact with the inner wall of the housing. In this case, the internal cavity of the insertion guide 131 may also be formed to be inclined.

Figure 17:
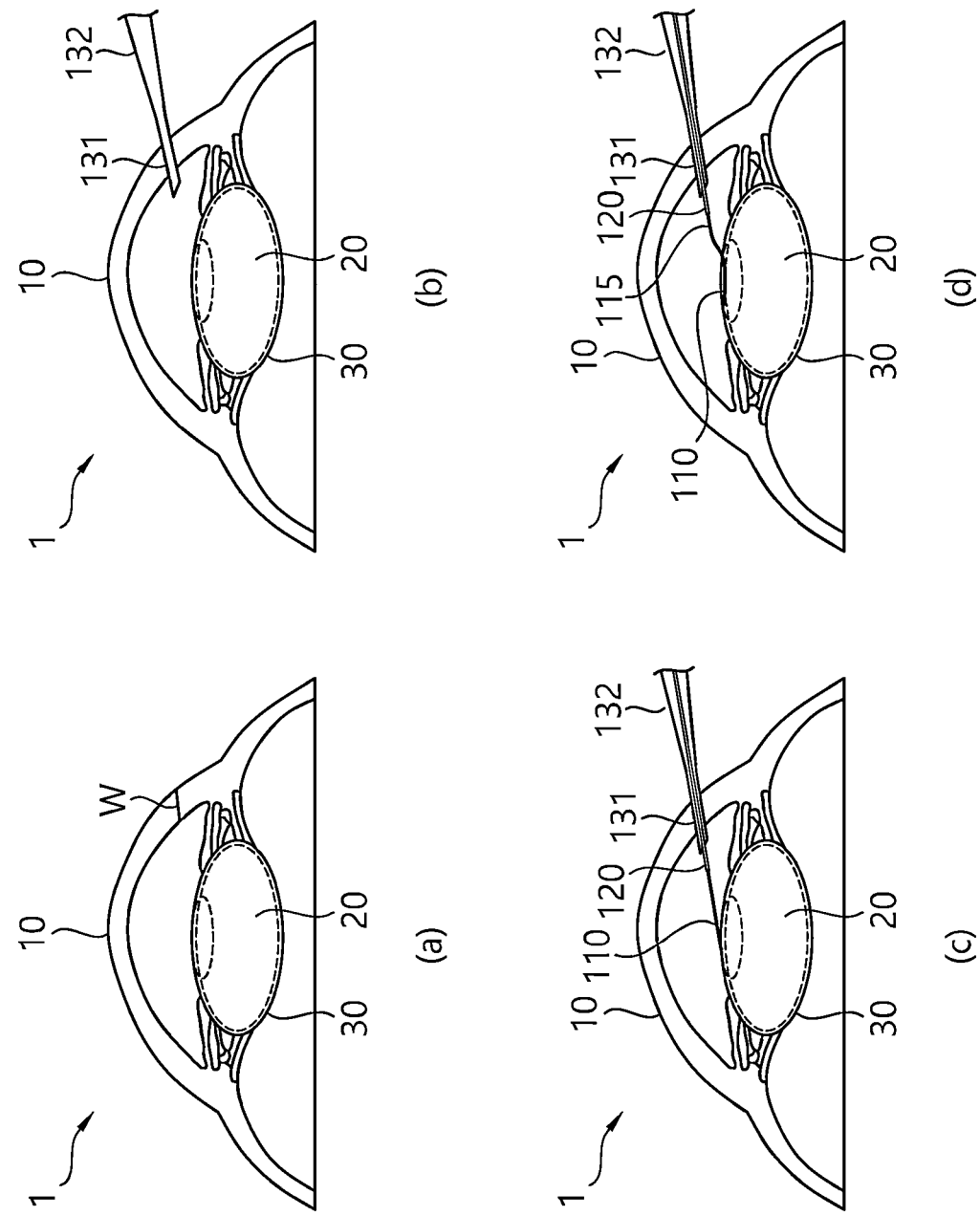
FIG. 17 is a view schematically illustrating a process in which a capsulorhexis device is inserted into an anterior chamber of the eye to make an incision in a crystalline lens capsule according to an embodiment of the present disclosure.
Figure 18:
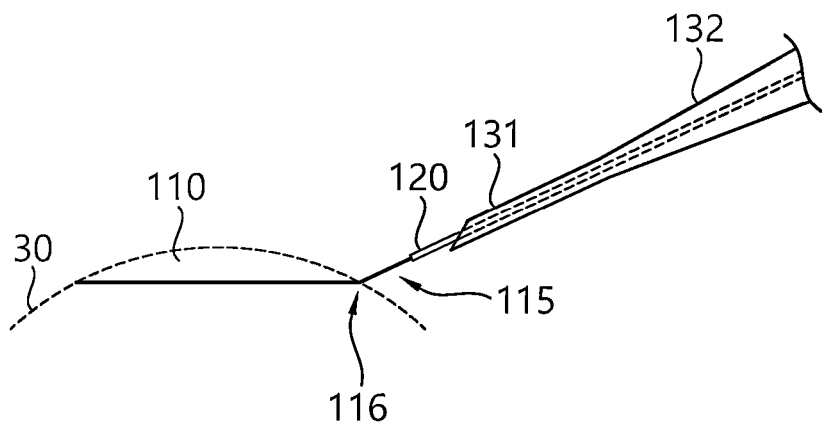
FIG. 18 is a detailed lateral cross-sectional view of the arrangement of the loop (110) and the moving member when the loop is adjusted to fully come in contact with a surface of an anterior capsule in a state in which the loop is inserted into the anterior chamber of the eye to make an incision in the anterior capsule.

A method of making an incision in a crystalline lens capsule using the capsulorhexis device according to an embodiment of the present disclosure will be described with reference to FIGS. 13, 17, and 18. The method includes preparing the capsulorhexis device in which the loop 110 is stored in the housing 132, forming an incision site in a cornea, inserting a front end of the insertion guide 131 into the incision site, sliding the moving member and the loop 110 from the housing so that the loop 110 passes through the insertion guide 131 and is unfolded into the anterior chamber of the eye, finely adjusting an angle of the capsulorhexis device to bring the curved part of the loop 110 in close contact with a crystalline lens capsule, applying a high frequency to make an incision in the tissue of the crystalline lens capsule using the circular curved part of the loop 110, and sliding the loop 110 into the insertion guide 131 again. Each of the steps will be described in detail below.

As illustrated in FIG. 13C, the loop 110 for making an incision has one end pressed and fixed to the moving member 120 having rigidity so as to be laterally supported and is stored in the housing 132. The housing 132 having an inner space connected to the insertion guide 131 has an inner space sufficient for storing the loop 110 without causing deformation thereof. A capsulorhexis device in a new condition in which the loop 110 is stored in the housing as in FIG. 13C is prepared.

First, as illustrated in FIG. 17A, in order to make an incision in the crystalline lens capsule, an incision site is formed at one side of the cornea 10. Here, preferably, an incision is made in a site that is adjacent to an edge of the cornea and is at the same height as or slightly higher than a surface of the anterior capsule.

As illustrated in FIG. 17B, one end of the insertion guide 131 is inserted into the incision site.

FIG. 17C is a lateral cross-sectional view of a state in which the loop 110 is unfolded into the anterior chamber of the eye through the insertion guide 131 when the operator moves the sliding button 141 forward in a state in which at least a portion of the insertion guide 131 is inserted. Here, the loop 110 is unfolded to be coplanar with the moving member 120, and the front end of the loop 110, that is, a front end of the curved part of the loop 110 comes in contact with the upper surface of the anterior capsule. Here, when an angle of insertion and an extent of insertion of the insertion guide 131 are appropriately controlled, it is easy to, as illustrated in FIG. 17C, bring the front end of the unfolded loop 110 in contact with a target point on the surface of the anterior capsule, which is at the opposite side of the incision site, from the center of the anterior capsule.

Meanwhile, FIG. 13 only illustrates the capsulorhexis device, and FIG. 13A illustrates an upper view of a state in which the moving member and the loop 110 further slide forward from the state illustrated in FIG. 13B and the entire loop 110 and the front end of the moving member pass through the insertion guide 131 such that the loop 110 is unfolded.

Since the moving member 120 slides on a plane parallel to the upper surface and/or the lower surface of the insertion guide 131 and the loop 110 is unfolded on the plane, through little training, the operator may easily set an incision site first and adjust the extent of insertion of the insertion guide while looking at the outer upper surface of the insertion guide to bring the front end of the loop 110 in contact with a desired target position. In this state, when the operator applies some force to press the loop 110 downward, the curved part comes in full contact with the surface of the anterior capsule. FIGS. 18 and 17D are enlarged views of the anterior capsule incision device and only the front surface of the crystalline lens capsule. As illustrated in FIG. 18, when the insertion guide 131 is slightly tilted, due to flexibility and elasticity of the support part of the loop 110, the portion 116 thereof where the support part and the curved part are connected is bent, and thus the curved part comes in full contact with the anterior capsule. In this way, using a simple structure without a separate bent structure, the operator may easily bring the loop 110 in contact with the surface of the anterior capsule while maintaining the circular shape of the loop 110.

Then, when power is turned on and a high frequency is applied to the loop 110 through the moving member, a circular incision is fully made in the anterior capsule at one time even without moving the device. Then, the sliding button is pushed rearward to move the loop 110 and the moving member into the insertion guide 131 again.

Figure 11:
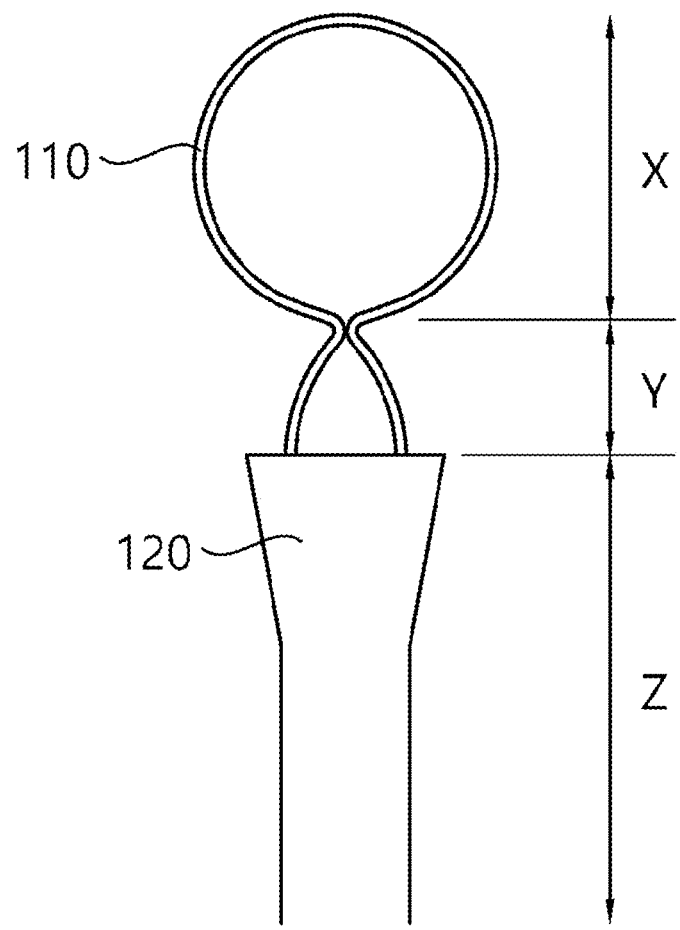
FIGS. 11 and 12 are conceptual diagrams for describing thicknesses and application areas of a coating that vary for the loop (110) and a moving member (120) according to an embodiment of the present disclosure.
Figure 12:
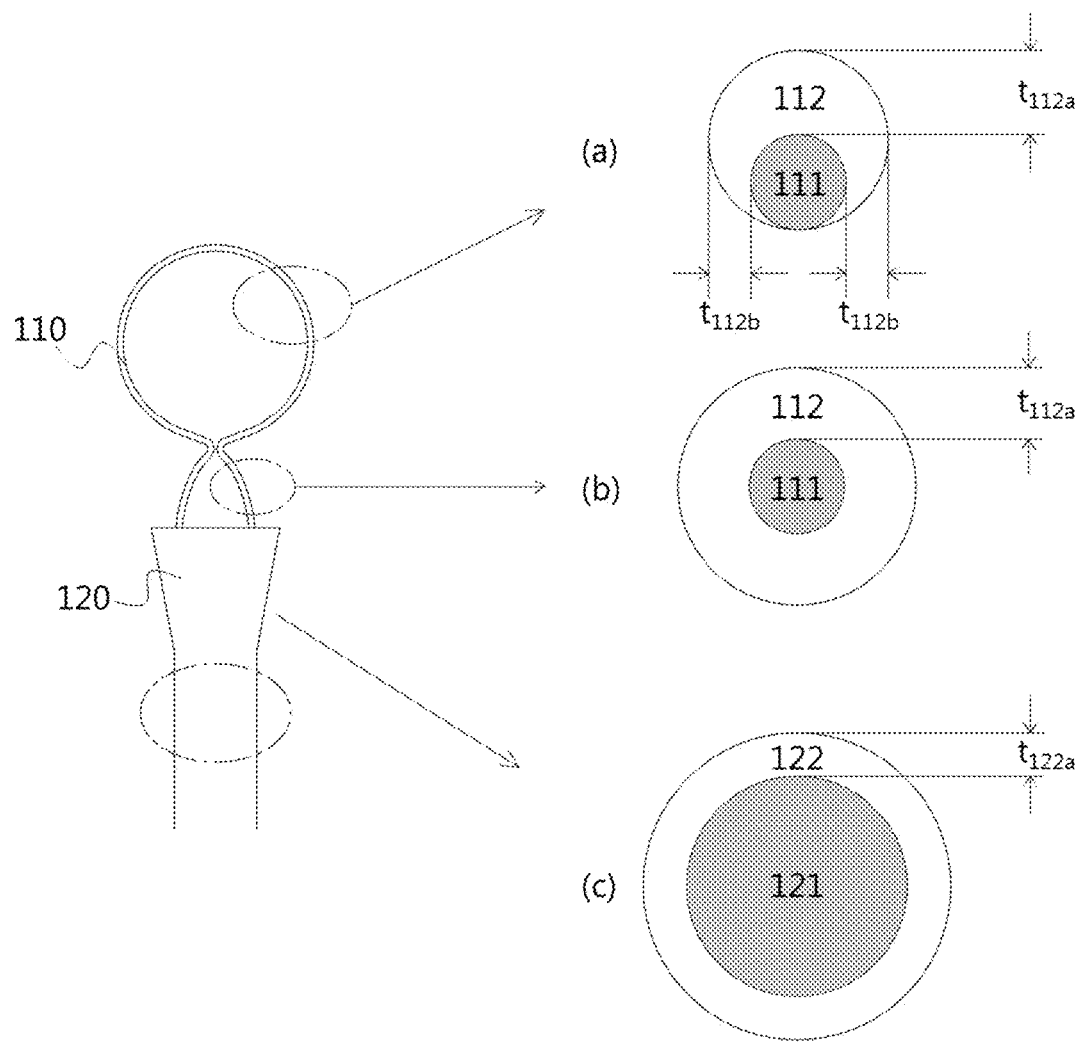

FIGS. 11 and 12 are conceptual diagrams for describing thicknesses and application areas of a coating that vary for the loop 110 and the moving member 120 according to an embodiment of the present disclosure. According to an embodiment of the present disclosure, in order to efficiently transfer energy to the loop 110 and to prevent leakage of energy in the energy transfer process, an insulator coating applied to the curved part (X) and the support part (Y) of the loop 110 and to the moving member 120 (Z) may be implemented to have a thickness that varies according to the application area.

More specifically, the curved part (X) of the loop 110 is an area that comes in contact with the front surface of the crystalline lens capsule 30 to make an incision in the anterior capsule 30, the coating part 112 may be applied to the circumference of each of the left side, right side, and upper side of the curved part (X), and the thickness of the coating part 112 may be implemented to be different for the circumference of each of the left side, right side, and upper side of the curved part (X) (for example, as illustrated in FIG. 3). Also, a coating part having substantially the same thickness as the coating on the curved part (X) may be applied to the support part (Y) of the loop 110, but while the coating part 112 is applied to the circumference of each of the left side, right side, and upper side of the curved part (X), a coating part 122 may be applied to the entire circumference of the support part (Y). In this way, since the coating part is applied to the curved part (X) except for the lower side thereof (that is, a portion thereof coming in contact with the anterior capsule) and the coating part is applied to the entire circumference of the support part (Y), leakage of electrical energy is blocked at those portions to allow a perfectly-circular incision to be made when making an incision in the anterior capsule.

The coating part may also be formed only as much as a predetermined length on the front end of the moving member 120 instead of being formed on the entire moving member 120 according to an embodiment of the present disclosure. The moving member 120 may consist of a pipe 121 at the center and the coating part 122 that covers the entire outer portion of the pipe 121, and according to a coating material, the thickness of the coating part 122 of the moving member 120 may be the same as or smaller than the thickness of the thickness of the coating part 112 of the loop 110.

FIG. 12 illustrates implementation examples of applying a coating. FIG. 12A illustrates an implementation example of coating on the curved part (X) of the loop 110, FIG. 12B illustrates an implementation example of coating on the support part (Y) of the loop 110, and FIG. 12C illustrates an implementation example of coating on the moving member 120. The thickness of the coating part 112 applied to the left side, right side, and upper side of the curved part (X) of the loop 110, the thickness of the coating part 112 on the support part (Y) of the loop 110, and the thickness of the coating part 122 on the moving member 120 may be different according to the coating composition. In FIG. 12C, $t_{122a}$ may be a thickness that is appropriate for efficiently transferring energy to the loop 110 and preventing leakage of energy in the energy transfer process and that is less than $t_{112a}$ according to the coating material.

As in the enlarged view in FIG. 3, the circular coating part 112 formed on the curved part of the loop may be located so that the center of the coating part 112 is above the center of the rope part 111. Thus, only the lower end of the rope part may be naturally exposed.

Figure 16:
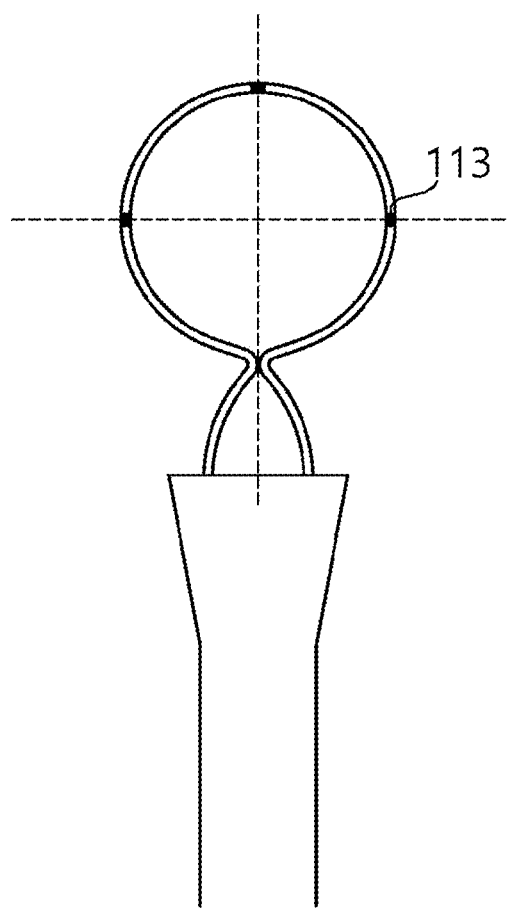
FIG. 16 is a conceptual diagram for describing a marker (113) of a loop (110) according to an embodiment of the present disclosure.

FIG. 16 is a conceptual diagram for describing a marker 113 of the loop 110 according to an additional embodiment of the present disclosure. As illustrated in FIG. 16, in the loop 110 according to the additional embodiment of the present disclosure, some areas of the curved part (X), more specifically, transverse and longitudinal central portions of the coating part 112 of the loop 110 may be marked with a predetermined marker, and accordingly, while the operator is making an incision in the crystalline lens capsule, the predetermined marker may aid the operator in finding the center of the loop 110.

For reference, in cataract surgery, generally, continuous curvilinear capsulorhexis (CCC) is performed on a dilated pupil. Since pupils dilate asymmetrically in some cases and it is difficult to maintain an accurate central point during CCC, once surgery begins, the operator hardly refers to important functional axes of eyes including the optical axis. However, maintaining an accurate central point is important not only for a multifocal artificial crystalline lens, whose use is on the rise, but also for a unifocal artificial crystalline lens, and as illustrated in FIG. 16, the coating part may be marked with reference markers for injection of an artificial crystalline lens to aid in maintaining the central point (centration) and to provide an advantage in injecting a multifocal artificial crystalline lens or another unifocal artificial crystalline lens.

Figure 14:
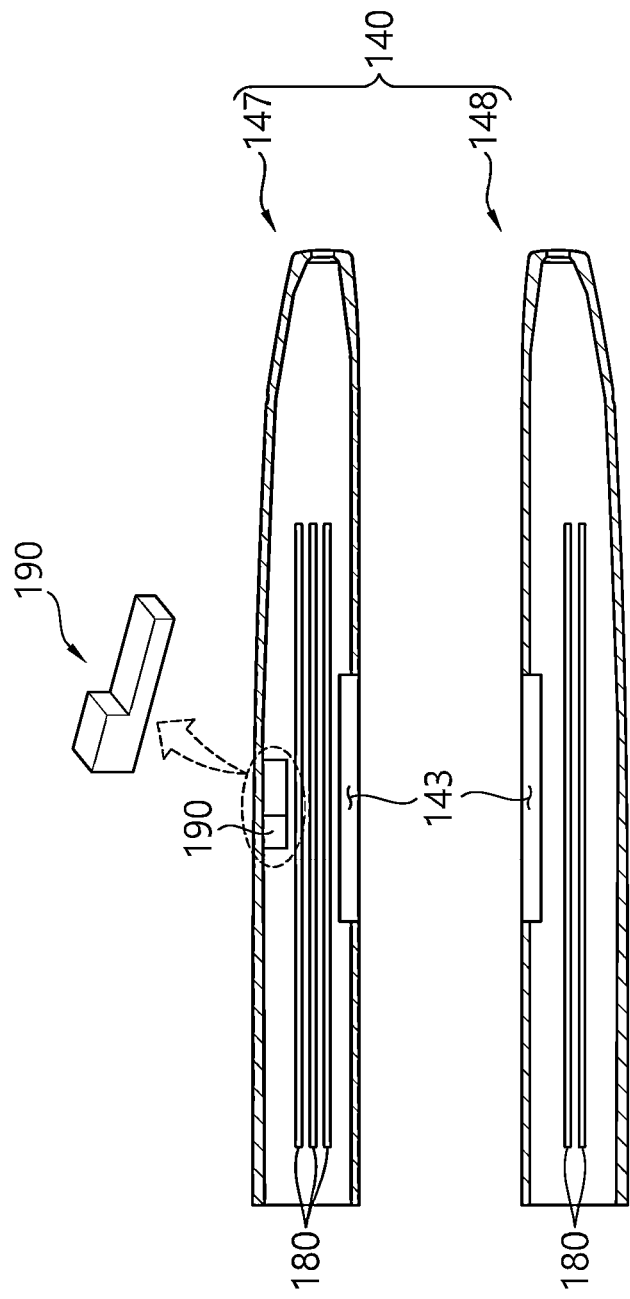
FIG. 14 is a plan view illustrating an internal structure of a body (140) according to an embodiment of the present disclosure.

Meanwhile, configurations of the body 140 and the holder 170, a guide rail 180, and a leaf spring 171 that are installed in the body will be described in detail with reference to FIGS. 14 and 15.

According to an embodiment of the present disclosure, the body 140 is formed due to coupling of two covers 147 and 148. The slot 143 is formed to be long on one side of each of the covers 147 and 148 so that the sliding button 141 is fitted and coupled to the slot 143 and moves along the slot to slide the loop 110 and the moving member 120.

The holder 170 on which the moving member 120 is mounted and which is coupled to the sliding button is installed in the body 140, and the other end of the moving member 120 is fixed and coupled to the holder 170 and linearly slides together with the holder 170 due to the sliding button.

The guide rail 180 configured to guide linear movement of the holder 170 is formed inside the body. Since the holder moves while being fitted to the guide rail, the linear movement of the moving member coupled to the holder 170 may become more stable.

A protruding part 190 having a step is formed on an inner wall of the body, and the leaf spring 171 is provided at one side of the holder 170. A side surface of one end (distal end) of the leaf spring 171 is fixed to a side surface of the holder 170, and a rear end of the leaf spring that extends to be inclined outward from the distal end thereof is configured as a free end. The leaf spring may also be integrally formed with the holder 170.

As illustrated in FIG. 15A, when the loop 110 is stored in the housing, the leaf spring may be disposed behind the protruding part 190 or disposed to come in contact with a rear end of the protruding part 190 to prevent unintentional sliding of the moving member and allow the loop 110 to be stored while the circular shape thereof is maintained. In particular, although the capsulorhexis device may be stored in an upright state and the holder, the moving member, and the loop 110 may move due to gravity, movement due to a weak external force is prevented by the protruding part 190 and the leaf spring.

Unlike in the drawings, the leaf spring may also be disposed further behind the protruding part without coming in contact therewith. Even in this case, when the holder 170 moves due to gravity and the side surface of the leaf spring coupled to the holder 170 comes in contact with the rear end of the protruding part 190, further movement of the holder 170 is prevented, and the loop 110 is stored while the circular shape thereof is maintained.

When the user intentionally moves the sliding button coupled to the holder 170, to which the moving member is fixed, with a predetermined force or more, the leaf spring may be pressed toward the holder and move together with the holder along a side surface of the protruding part 190. This process corresponds to a process in which the user slides the loop 110, which has been stored in the housing, toward the insertion guide 131.

Then, after the rear end of the leaf spring is caught at a front end of the protruding part 190, rearward movement of the moving member and the holder 170 is prevented. A position where the rearward movement is prevented corresponds to a position where the moving member and the loop are inserted into the insertion guide but may also be set to correspond to a position where deformation of the loop begins. The positions and lengths of the moving member, the holder, and the loop may be adjusted to correspond to a position where the rear end (free end) of the leaf spring is caught at the protruding part. That is, the loop 110 inserted into the insertion guide at least one time is not able to return to a storage position in the housing and may only be unfolded and/or inserted into the insertion guide. In this way, from looking at the position of the loop 110, the user may easily recognize whether the capsulorhexis device, which has been used one time, is about to be reused.

Basically, since the device is disposable to prevent infection or the like, whether the device has been used may be easily determined by the above structure.

According to the capsulorhexis device according to an embodiment of the present disclosure, a problem in that one side of the loop 110 sliding in the insertion guide 131 is twisted and permanently deformed may be prevented, and accordingly, the loop 110 is allowed to, after passing through the insertion guide 131, be unfolded on a single plane without being deformed and neatly make a perfectly-circular incision in a crystalline lens capsule.

The loop 110 is configured to be coplanar with the moving member when stored in the housing, and while the loop 110 slides together with the moving member and passes through the insertion guide 131, at least a portion of the loop 110 deviates from the plane and forms a slope to control deformation to be distributed, and after the loop 110 passes through the insertion guide 131, the loop 110 is configured to be unfolded in a circular shape and disposed on the plane. The moving member is configured to linearly move on the same plane in the process in which the loop 110 is stored and slides.

The plane is parallel to the outer upper surface of the insertion guide 131, and the moving member slides along the central axis of the insertion guide 131 which has a tubular shape.

Exemplary embodiments have been disclosed herein and in the drawings. Although specific terms are used herein, the terms are only used for the purpose of describing the present disclosure and are not intended to limit meanings or limit the scope of the present disclosure defined in the claims below. Accordingly, those of ordinary skill in the art should understand that various modifications and other equivalent embodiments are possible from the embodiments disclosed herein. Therefore, the actual technical scope of the present disclosure should be determined by the technical idea of the attached claims.

The invention claimed is:

1. A capsulorhexis device configured to be inserted into an incision site of a cornea to make an incision in a crystalline lens capsule surrounding a crystalline lens, the capsulorhexis device comprising:
   a loop having elasticity and conductivity;
   a moving member having one end fixed and coupled to the loop;
   an insertion guide configured so that, while the incision is being made in the crystalline lens capsule, a front end thereof is inserted into the incision site of the cornea; and
   a housing having one end coupled to a rear end of the insertion guide,
   wherein the loop is housed in the housing and, to make the incision in the crystalline lens capsule, slides in the housing together with the moving member to pass through the insertion guide and be deployed into an anterior chamber of the eye;
   wherein the loop is configured to be placed on a virtual plane same as the moving member when housed in the housing, and at least a portion of the loop deviates from the virtual plane while the loop slides together with the moving member and passes through the insertion guide;
   wherein the loop is deployed into a circular shape and located on the virtual plane after passing through the insertion guide; and
   wherein the moving member is configured to linearly move on the virtual plane, on which the moving member is housed in the housing, while the loop slides, the moving member being housed in the housing on the plane.

2. The capsulorhexis device of claim 1, wherein:
   the loop consists of a support part having one end coupled to the moving member and a curved part extending from the other end of the support part to form the loop in a circular shape; and
   the loop is housed in the housing without being deformed by an external force, is deformed while passing through the insertion guide to make the incision in the crystalline lens capsule, and then is deployed and restored to the circular shape after passing through the insertion guide.

3. The capsulorhexis device of claim 2, wherein the curved part of the loop is marked with a marker to assist an operator in finding a center of the loop.

4. The capsulorhexis device of claim 1, wherein:
   the virtual plane is parallel to an outer upper surface of the insertion guide; and
   the moving member is configured to slide along a central axis of the insertion guide which has a tubular shape.

5. The capsulorhexis device of claim 1, wherein:
   an outer upper surface of the insertion guide is formed to be parallel to the plane on which the moving member is disposed; and
   an internal cavity of the insertion guide is formed to be long and have a left-right symmetrical cross-section, a central axis connecting the left and right sides of the symmetrical cross-section is formed to be inclined at a predetermined angle with respect to the virtual plane, and the loop is deformed as the loop moves along an inner wall of the internal cavity while passing through the internal cavity.

6. The capsulorhexis device of claim 1, wherein:
   an outer surface of the insertion guide is formed in a long tubular shape having a left-right symmetrical cross-section; and
   an internal cavity of the insertion guide is formed to be left-right symmetrical about an axis along which the loop slides and formed to have a slope at a predetermined angle with respect to the virtual plane.

7. The capsulorhexis device of claim 1, wherein the loop consists of:
   a rope part in which a plurality of conductive wires are formed to be twisted in the shape of a straw rope to have elasticity; and
   an insulating coating part configured to coat at least one area of the rope part.

8. The capsulorhexis device of claim 1, wherein the loop has an elliptical shape when disposed in the housing, and the elliptical shape is an elliptical shape in which a diameter in a direction perpendicular to a direction in which the loop slides is larger than a diameter in the direction in which the loop slides.

9. The capsulorhexis device of claim 1, wherein:
   the loop consists of a support part having one end coupled to the moving member and a curved part coupled to the other end of the support part; and an axis along which the moving member slides is the same as a central axis of the insertion guide.

10. A capsulorhexis device configured to be inserted into an incision site of a cornea to make an incision in a crystalline lens capsule surrounding a crystalline lens, the capsulorhexis device comprising:
a loop having elasticity and conductivity;
a moving member having one end fixed and coupled to the loop;
an insertion guide, which is a nozzle, configured so that, while the incision is being made in the crystalline lens capsule, a front end thereof is inserted into the incision site of the cornea; and
a housing having one end coupled to a rear end of the insertion guide,
wherein the loop is housed in the housing and, to make the incision in the crystalline lens capsule, can slide in the housing together with the moving member to pass through the insertion guide and be deployed into an anterior chamber of the eye;
wherein the loop is configured to be placed on a virtual plane same as the moving member when housed in the housing;
wherein an outer surface of the insertion guide is formed in a long tubular shape having a left-right symmetrical cross-section; and
wherein an internal cavity of the insertion guide is formed to be left-right symmetrical about an axis along which the loop slides and formed to have a slope at a predetermined angle with respect to the virtual plane.

11. A capsulorhexis device comprising:
a loop having elasticity and conductivity;
a moving member having one end fixed and coupled to the loop;
an insertion guide, which is a nozzle, configured so that, while the incision is being made in the crystalline lens capsule, a front end thereof is inserted into the incision site of the cornea; and
a housing having one end coupled to a rear end of the insertion guide,
wherein the loop is housed in the housing and, to make the incision in the crystalline lens capsule, can slide in the housing together with the moving member to pass through the insertion guide and be deployed into an anterior chamber of the eye,
wherein:
a pair of guide channels, formed along a direction in which the loop slides, is provided inside the housing, and
the pair of guide channels consists of a first guide channel configured to allow one area of the loop to slide with being pressed downward and a second guide channel configured to allow another area of the loop to slide with being supported upward.

12. A capsulorhexis device configured to be inserted into an incision site of a cornea to make an incision in a crystalline lens capsule surrounding a crystalline lens, the capsulorhexis device comprising:
a loop having elasticity and conductivity;
a moving member having one end fixed and coupled to the loop;
an insertion guide, which is a nozzle, configured so that, while the incision is being made in the crystalline lens capsule, a front end thereof is inserted into the incision site of the cornea; and
a housing having one end coupled to a rear end of the insertion guide,
wherein the loop is housed in the housing and, to make the incision in the crystalline lens capsule, can slide in the housing together with the moving member to pass through the insertion guide and be deployed into an anterior chamber of the eye,
wherein capsulorhexis device further comprises a body that is coupled to the other end portion of the housing and has a sliding button provided to slide the loop and the moving member,
wherein a holder on which the moving member is mounted and which is coupled to the sliding button is installed in the body, and the other end of the moving member is fixed and coupled to the holder and linearly slides together with the holder by using the sliding button;
wherein a protruding part is formed on an inner wall of the body, a leaf spring is provided with the holder, and when the loop is stored in the housing, the leaf spring is disposed at a rear end of or at a rear of the protruding part to prevent unintentional sliding of the moving member and thereby allow the loop to be stored with the circular shape thereof being maintained;
wherein when the sliding button coupled to the holder, to which the moving member is fixed, is moved with a predetermined force or more, the leaf spring moves along one surface of the protruding part; and
wherein after a rear end of the leaf spring is caught at a front end of the protruding part, rearward movement of the moving member and the holder is prevented.

13. A capsulorhexis device, which is a capsulorhexis device inserted into an incision site of a cornea to make an incision in a crystalline lens capsule surrounding a crystalline lens, the capsulorhexis device comprising:
a loop having elasticity and conductivity;
a moving member having one end fixed and coupled to the loop;
a head part including a housing configured to store the loop therein and an insertion guide coupled to one end portion of the housing to communicate therewith; and
a body that is coupled to the other end portion of the housing and has a sliding button provided to slide the loop and the moving member through the head part,
wherein, to make the incision in the crystalline lens capsule, a front end of the insertion guide is configured to be inserted through an incision site of a cornea, the head part provides a path along which the loop is moved to the outside through the insertion guide, and the loop slides to pass through the insertion guide from the housing, is unfolded into an anterior chamber of the eye that is below the cornea, and is configured to, using high-frequency power supplied thereto, make a circular incision in a site of the crystalline lens capsule that comes in contact with the loop;
wherein the loop is configured to be placed on a virtual plane same as the moving member when housed in the housing, and at least a portion of the loop deviates from the virtual plane while the loop slides together with the moving member and passes through the insertion guide;
wherein the loop is deployed into a circular shape and located on the virtual plane after passing through the insertion guide; and
wherein the moving member is configured to linearly move on the virtual plane, on which the moving member is housed in the housing, while the loop slides, the moving member being housed in the housing on the plane.

14. The capsulorhexis device of claim 13, wherein:
the loop consists of a support part having one end coupled to the moving member and a curved part extending from the other end of the support part to form the loop in a circular shape; and
the loop is stored in the housing without being deformed due to an external force, is deformed while passing through the insertion guide to make the incision in the crystalline lens capsule, and then is unfolded and restored to the circular shape after passing through the insertion guide.

\* \* \* \* \*